United States Patent [19]

Ngo

[11] Patent Number: 4,981,961
[45] Date of Patent: Jan. 1, 1991

[54] SYNTHETIC AFFINITY LIGAND COMPOSITIONS AND METHODS FOR PURIFICATION AND RECOVERY OF ORGANIC MOLECULES

[75] Inventor: That T. Ngo, Irvine, Calif.

[73] Assignee: BioProbe International, Inc., Tustin, Calif.

[21] Appl. No.: 404,917

[22] Filed: Sep. 8, 1989

Related U.S. Application Data

[63] Continuation-in-part of Ser. No. 243,352, Sep. 12, 1988, abandoned.

[51] Int. Cl.$^5$ .................... C12N 11/06; C08F 283/00; A61K 39/395
[52] U.S. Cl. .................................. 536/112; 435/178; 435/179; 435/180; 435/181; 435/182; 435/270; 435/815; 436/529; 436/530; 436/531; 436/532; 436/535; 546/258; 530/387; 530/830; 530/809; 530/816; 536/124; 536/126
[58] Field of Search ............. 536/112, 124, 126; 435/178, 179, 180, 181, 182, 270, 815; 436/529, 530, 531, 532, 535; 546/356; 530/387, 830, 809, 816

[56] References Cited

U.S. PATENT DOCUMENTS

| 4,415,665 | 11/1983 | Mosbach et al. | 435/179 |
| 4,582,875 | 4/1986 | Ngo | 435/178 |
| 4,704,366 | 11/1987 | Juarez-Salinas et al. | 530/402 |
| 4,801,687 | 1/1989 | Ngo | 514/8 |
| 4,886,755 | 12/1989 | Ngo | 435/178 |

Primary Examiner—Ronald W. Griffin
Attorney, Agent, or Firm—Nilsson, Robbins, Dalgarn, Berliner, Carson & Wurst

[57] ABSTRACT

A novel class of compounds, methods for the preparation thereof and the use thereof in chromatographic methods for binding various biologically active materials non-covalently are disclosed. The class of compounds comprises the reaction product of a polymeric gel with a pyridine base, such as 4-dimethylaminopyridine (DMAP), and a halogen-substituted pyridine, such as 3,5-dichloro-2,4,6-trifluoropyridine (DCTFP), which reaction product may in turn be optionally reacted with hydroxyl ions or specified low-molecular-weight compounds. These compounds are capable of selectively and efficiently binding proteins and other organic materials of interest non-covalently to a degree comparable or superior to the heretofore preferred natural affinity ligands, such as Protein A gels. The novel compounds find particular utility in purification and recovery of proteins such as serum albumin and immunoglobulins of various classes from crude sources, such as diluted serum samples from various species.

38 Claims, 12 Drawing Sheets

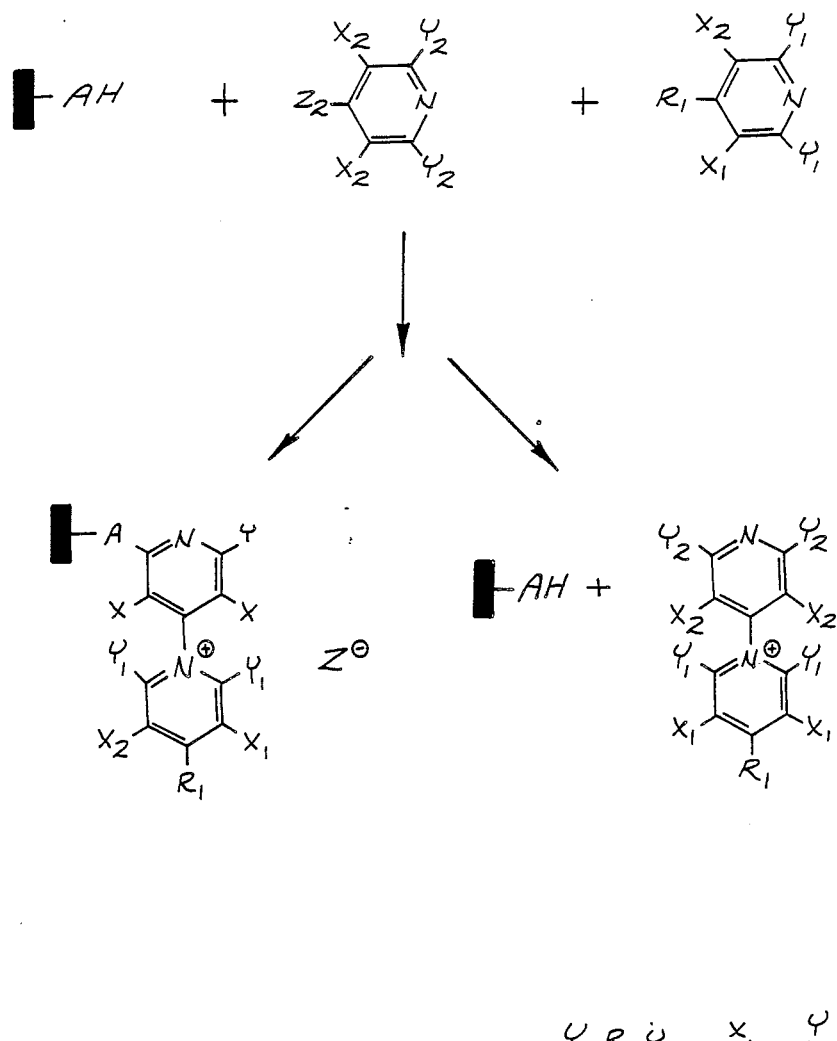
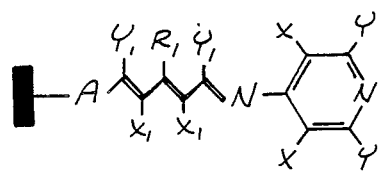
FIG. 1

1 2 3 4 5 6 7 8

HUMAN 1 2 3 4 5 6 7 8

MOUSE 1 2 3 4 5 6 7 8

RABBIT 1 2 3 4 5 6 7 8

BOVINE 1 2 3 4 5 6 7 8

CHICKEN 1 2 3 4 5 6 7 8

GOAT 8 7 6 5 4 3 2 1

MOUSE 1 2 3 4 5 6 7 8

PIG 1 2 3 4 5 6 7 8

RABBIT 1 2 3 4 5 6 7 8

RAT

SYNTHETIC AFFINITY LIGAND COMPOSITIONS AND METHODS FOR PURIFICATION AND RECOVERY OF ORGANIC MOLECULES

FIELD OF THE INVENTION

This application is a continuation-in-part of Ser. No. 07/243,352 filed Sept. 12, 1988, now abandoned.

This invention relates to a method of covalently binding organic ligands to polymeric carriers. In one of its more particular aspects the invention relates to a new method of covalently binding organic ligands containing one or more nucleophilic group such as amino, hydroxyl or sulfhydryl groups to polymeric gels.

This invention also relates to compositions and methods for separation and purification of proteins and other organic molecules, particularly those of biochemical interest, through the use of synthetic affinity ligands. In another of its more particular aspects, the present invention relates to methods and compositions for purification and recovery of specific organic molecules of biological interest, and in particular proteins such as immunoglobulins, through the use of a non-peptido, Protein A and/or Protein G mimetic ligand (i.e., immunoglobulin-binding ligand) bound to a polymeric gel, and to methods for preparation of such non-peptido, Protein A mimetic ligands.

BACKGROUND AND SUMMARY OF THE INVENTION

Polymers such as polysaccharides, polyvinyl alcohol and Nylon are widely used as solid supports for immobilizing enzymes and for preparing biospecific affinity matrices. Several methods are known for coupling biologically active ligands to water insoluble carriers. These methods have been used for the covalent immobilization of biologically active materials such as enzymes, antibodies or antigens. Immobilized biologically active materials find use in many different fields of technology. One example thereof is in immunologic determination methods. Another important application is in affinity chromatography, wherein an organic ligand having biospecific affinity to some other organic substance has been bonded to a water insoluble polymeric carrier. Proteins have been bonded to water soluble polymers as well as water insoluble polymers for modifying the properties of the protein.

Prior to development of the compositions and methods disclosed and claimed in Ser. No. 07/243,352, the entire disclosure of which is hereby incorporated by reference, no method had been found for preparing an activated polymeric support capable of effectively coupling a ligand at an acidic pH, for example at a pH less than about 4. Since some ligands must be coupled in the acidic pH range, the need arises for an activating agent which can produce activated polymers effective in the acid range of pH. Pepsin, for example, must be coupled at a pH of below about 4 because it is denatured and loses its enzymatic activity at a higher pH.

Ser. No. 07/243,352 has as its principal object methods and compositions for use in providing stable and hydrolysis-resistant coupling products of polymeric carriers and organic ligands. A particular object of that application is to provide chromatographic matrices which can be used to bind various organic molecules, and in particular biologically active materials, both covalently and non-covalently.

In accordance with the disclosure of Ser. No. 07/243,352 these and other objects are achieved by forming an "activated" derivative of a polymeric carrier by reacting the polymer with a substituted 2-halopyridine (as therein defined) in the presence of an organic base and then reacting the substituted polymer with a ligand containing one or more nucleophilic groups (such as amino, hydroxyl or sulfhydryl group). The method according to the invention of Ser. No. 07/243,352 thus comprises an activation step, wherein a substituted 2-halopyridine is introduced into a polymeric carrier, and a coupling step, in which an organic ligand is bonded covalently to the polymeric carrier. The preparation of several products believed generally useful in non-covalently binding organic molecules, and in particular proteins (such as serum albumin and immunoglobulins), is disclosed therein.

The development of compositions useful in the non-covalent binding of organic molecules is of tremendous significance to the chemical and biological arts, particularly when such compositions exhibit any degree of binding selectivity. For example, in spite of the widespread development and use of ion-exchange resins and Protein A affinity gels for separation and purification of organic materials of biological interest (such as, in particular, polyclonal and monoclonal antibodies as used in diagnostics, purification and experimental therapeutics), there remain several disadvantages inherent in these methods. The ion-exchange chromatographic method, due to its lack of specificity, requires in general the use of several columns and gradient elution procedures involving specific detection methods to monitor the process. On the other hand, while Protein A affinity gels are somewhat more specific, they are significantly more expensive than ion-exchange chromatography. Moreover, Protein A gels are unable to bind significant amounts of IgG from rats, goats or chickens. There is also the possibility of immune reactions due to Protein A inadvertently leaked into recovered antibody preparations, which may limit the value of chromatographic methods using Protein A gels for purification of materials with which binding does occur. Finally, immobilized Protein A gels are susceptible to microbial and protease degradation, as well as to other protein denaturing agents.

Therefore, it would clearly be desirable to develop a chromatographic support with a synthetic ligand, preferably one of low molecular weight and low cost, which would be capable of selectively and efficiently binding molecules of biological interest, and in particular, of binding antibodies from all species.

The development of thiophilic gels by Porath et al. is an effort directed toward this end [see, e.g., Porath J. et al, "A New Kind of 'Thiophilic' Electron-Donor-Acceptor Adsorbent," Makromol. Chem., Macromol. Symp. 17: 359–71 (1988) and references cited therein]. In thiophilic interaction chromatography, antibody is adsorbed on a thiophilic gel in the presence of high concentrations of neutral water-structure-forming salts. Desorption is achieved by elution with buffer not containing the salts. The partial structure of a thiophilic gel may be illustrated as

$-O-CH_2-CH_2-$ $CH_2-SO_2-CH_2-CH_2-S-CH_2-CH_2-OH$, wherein

-continued

P wherein represents the polymer backbone.

It is an object of the present invention to provide additional synthetic ligands capable of selectively and efficiently binding materials of interest from a variety of different sources.

The present invention has as its principal object providing a stable and hydrolysis-resistant coupling product of a polymeric carrier and an organic ligand.

Another object of the present invention is to provide such a process which can be conducted under relatively mild conditions in order to avoid any detrimental effect upon reactants such as sensitive biological ligands.

Another object of the present invention is to provide a series of activating agents which can be reacted with polymeric carriers to produce an activated polymer capable of being coupled to a wide variety of organic ligands at a wide pH range.

Another object of this invention is to provide chromatographic matrices which can be used to bind various biologically active materials both covalently and non-covalently.

It is also a further object of the present invention to develop materials capable of selective binding of antibodies from all species, including those from rats, goats and chickens heretofore not amenable to treatment using conventional purification methods employing Protein A affinity ligands.

It is yet a further object of the present invention to provide synthetic affinity ligands capable of adsorbing organic molecules of interest in general, and peptides such as serum proteins in particular, without the use of high salt concentrations in the adsorption process.

It is another object of the present invention to provide materials and processes for isolation and purification of immunoglobulins of various classes and from a variety of species without the use of proteinaceous materials which themselves could lead to contamination of the resulting product.

These and other objects of the invention are achieved in accordance with one aspect of the present invention by forming a reactive derivative of a polymeric carrier by reacting the polymer with a substituted 2-halopyridine as hereinafter defined and then reacting the activated polymer with a ligand containing one or more nucleophilic groups such as amino, hydroxyl or sulfhydryl group to form a coupled product.

The method according to this aspect of the present invention thus comprises an activation step, wherein a substituted 2-halopyridine is introduced into a polymeric carrier and a coupling step in which an organic ligand is bonded covalently to the polymeric carrier. The method may also comprise the use of the coupled product as a chromatographic matrix capable of binding various biologically active materials covalently or non-covalently, as desired.

The present invention is directed to a novel class of products, one method for the preparation of which is disclosed in Ser. No. 07/243,352, and to the use thereof in chromatographic methods for binding various biologically active materials non-covalently. In particular, the present invention is directed in another particular aspect thereof to the surprising discovery that members of a particular class of novel compounds which may be defined as the reaction product of a polymeric gel with a pyridine base, such as 4-dimethylaminopyridine (DMAP), and a halogen-substituted pyridine, such as 3,5-dichloro-2,4,6-trifluoropyridine (DCTFP), which reaction product may in turn optionally be reacted with other specified low-molecular-weight compounds or with a source of hydroxide ions, are capable of selectively and efficiently binding proteins and other organic materials of interest non-covalently to a degree comparable or superior to the heretofore preferred natural affinity ligands, such as Protein A gels.

In particular, it has now been determined that in accordance with one embodiment of the present invention, subsequent treatment of the reaction product of a Sepharose gel, DMAP and DCTFP with ethylene glycol leads to the formation of a product (hereinafter, "O-gel") which may be employed to achieve purification and recovery of proteins such as serum albumin and immunoglobulins of various classes from crude sources, such as serum samples from various species.

One type of method for the preparation of several members of this novel class of compounds is described in several examples of Ser. No. 07/243,352. The present invention is directed to attempts at elucidation of the structure of these compounds and exploitation of their exceptional utility in separation and purification of organic molecules, and in particular in the recovery of specific proteins in relatively pure form even from crude sources, such as serum samples.

BRIEF DESCRIPTION OF THE DRAWINGS

FIG. 1 illustrates a provisional assessment of the structure of the compounds of the present invention based on available information as to composition and a proposed reaction pathway for formation thereof.

DETAILED DESCRIPTION

Figure 2:
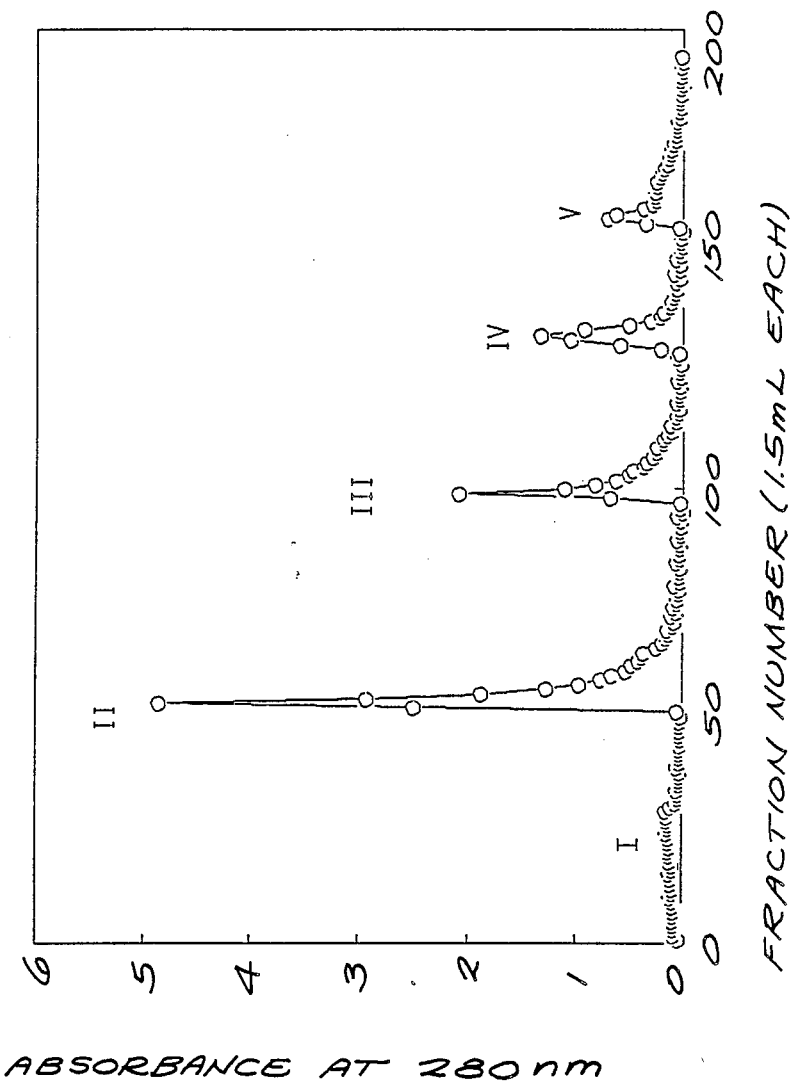
FIG. 2 is a chromatogram of the eluent recovered after treatment of diluted human serum in an O-gel column.

The polymeric carrier can be a water insoluble or water soluble polymeric substance. Except as indicated below, the choice of the carrier is not critical for carrying out the process of the present invention. In principle, any type of carrier can be used which has a polymeric nature and contains at least one nucleophilic group such as a hydroxyl, amino or sulfhydryl group bonded to a carbon atom which is available for activation and coupling. The carrier is chosen with regard to the requirements in the individual situation, primarily with regard to the type of ligand to be coupled and the intended use of the coupling product. The carrier may be comprised of natural, semi-synthetic or synthetic polymeric materials containing nucleophilic groups. Examples of important natural and semi-synthetic carrier materials are provided below with reference to a particular embodiment of the present invention; the enumerated carriers, as well as many others, are suitable for use in accordance with all aspects of the present invention.

The substituted 2-halopyridines which can be used as activating agents in the process of the invention are derivatives of 2-halopyridines in which at least one of the ring positions of the 2-halopyridine is substituted with an electron withdrawing group. The substituted 2-halopyridine can be represented by means of the structural formula:

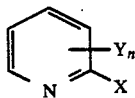

wherein X is F, Cl or Br, Y is F, Cl, Br, $NO_2$, $CH_3$, or $CF_3$, and n is 1 to 4. Where n is greater than 1, the substituents designated by Y may be the same or different. At least one of the substitutents designated by Y must be an electron withdrawing group.

Typical compounds include pentafluoropyridine (PFP), 3,5-dichloro-2,4,6-trifluoropyridine (DCTFP), 3,5-dinitro-2-chloropyridine (CDNP), 2,3,5-trichloropyridine (TCP), 2,6-difluoropyridine (DFP), 2-chloro-5-trifluoromethylpyridine (CTFMP), 2,3,5,6-tetrafluoro-4-methylpyridine (TFMP) and 2,3,5,6-tetrafluoropyridine (TFP).

The activation of nucleophile containing polymeric carriers can be carried out in the presence of a slight excess of a tertiary amine such as triethylamine, tributylamine or 4-dimethylaminopyridine (DMAP) in a polar organic solvent such as acetone, dimethylformamide (DMF), acetonitrile or tetrahydrofuran (THF). The substituted 2-halopyridines react with the polymeric carrier under ambient conditions of temperature and pressure, for example at about 22° to 35° C. in a time of about 0.1 to 2 hours. The resulting activated polymers, which react readily with primary or secondary amino, hydroxyl or sulfhydryl groups or various organic ligands, were found to be stable for at least four months when stored at 4° C. in acetone. The activated polymeric carrier can also be stored in dilute mineral acids such as 2 mM phosphoric acid, or in dry form, if desired.

The coupling method of the present invention is generally applicable to organic ligands containing the indicated amino, hydroxyl or sulfhydryl groups. Salts of sulfhydryl group containing compounds such as Na salts thereof are likewise useful for this purpose. In general, the product selected for coupling should be a nucleophile, so that the coupling reaction can be carried out smoothly. Thus, the ligand may contain any aliphatic, aromatic, heterocyclic, or heteroaromatic radical or any radical which is a combination of the foregoing, so long as the resulting ligand will have functional groups available for coupling.

One type of ligand of special interest includes biologically active ligands, for example, proteins, enzymes, antibodies, antigens, amino acids, nucleic acids, thiol compounds, cofactors, haptens and many other types of biologically active ligans which can be bound covalently to the activated polymeric carrier and used, for example, for affinity chromatographic purposes or in immunoassays or in biocatalysis.

Coupling of the ligand to the activated polymeric carrier can be accomplished under varying conditions of temperature and pH and can be performed in aqueous reaction media as well as in polar organic solvents. Reaction conditions are not critical for either the activation step or the coupling step and are primarily chosen with regard to the sensitivity of the reactant and to practical considerations of convenience. Mild reaction conditions are preferred. It is, for example, often suitable to work at ambient temperatures and pressures. The pH at which the coupling reaction is carried out can range from an acidic pH, for example, a pH less than about 4, to an alkaline pH, for example, a pH of about 10.

Unreacted activated groups remaining after coupling, which might impede further utilization of the coupled polymer, can be deactivated by suspending the coupled polymer in 0.2 M Tris-HCl, pH 9 or in 0.1M NaOH, at room temperature, for several hours. Other nucleophiles such as glycine or lysine can also be used for this purpose.

An outstanding advantage of this aspect of the present invention is that of providing chromatographic matrices characterized by a very stable chemical linkage between the affinity ligand and the solid matrix to which it is bound. If such stable chemical linkage is not formed, loss of the affinity ligand from the matrix can result in contamination of the purified material obtained by use of such chromatographic matrix and shortening of the useful life of the matrix. The method of this invention results in minimal detachment of affinity ligands even upon subsequent exposure to basic and nucleophilic buffers and thus provides superior chromatographic matrices.

Another advantage is the realization of significantly greater ligand binding capacity of the activated polymeric carrier than in the case of methods presently available.

The present invention is also directed in another particular aspect thereof to a novel class of products, one method for the preparation of several of which is described in Ser. No. 07/243,352, and to the use thereof as highly selective and efficient chromatographic adsorbents for the recovery and purification of organic materials, particularly those of biological interest. This class of materials may be employed, for example, in the separation and purification of immunoglobulins of various classes and from various species, permitting the recovery of the immunoglobulins in substantially purified form directly from crude sources, such as dilute, serum samples.

In accordance with this aspect of the present invention, this novel class of compounds comprises polymeric carriers with synthetic affinity ligands bound thereto. These compounds may be described as the reaction products of a nucleophile-containing polymeric carrier, a halogen-substituted pyridine (as hereinafter defined) and a pyridine base (as hereinafter defined). While the absolute structure of these novel compounds has not been resolved with certainty, it is believed that the compounds are represented by either of the general formulas I(a) or I(b):

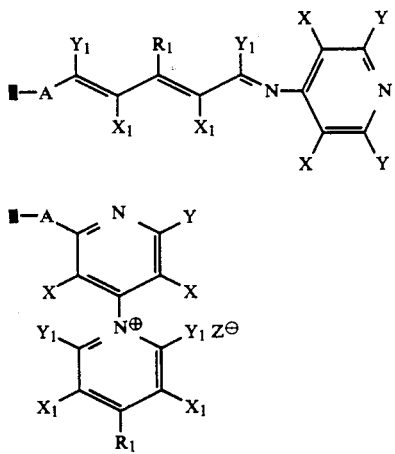

wherein

A is O, S or NR, in which R is hydrogen or optionally substituted alkyl, aryl or aralkyl;

each X is independently selected from the group consisting of halogen, trihalomethyl and nitro;

each Y is independently selected from the group consisting of halogen, hydroxyl, amino and $-A_1R_4$, in which $A_1$ is O, S or $NR_5$, $R_4$ is optionally substituted alkyl, aryl, or aralkyl, and $R_5$ is hydrogen or optionally substituted alkyl, aryl or aralkyl, with the proviso that at least one Y in Formula I(a) or Y in Formula I(b) is not halogen;

each of $X_1$ is hydrogen or optionally substituted alkyl, aryl or aralkyl;

at least one $Y_1$ is hydrogen and the other is hydrogen or optionally substituted alkyl, aryl or aralkyl;

$R_1$ is hydrogen, optionally substituted alkyl, aryl or aralkyl, or $-NR_2R_3$, in which $R_2$ and $R_3$ are the same or different and are optionally substituted alkyl, aryl or aralkyl; and ■- is a polymer.

In the context of this application, "alkyl" refers to straight- or branched-chain alkyl of one to about 20 carbon atoms, preferably from one to about eight carbon atoms, as well as aliphatic cyclic substituents (such as cyclopentyl and cyclohexyl); "aryl" refers to aromatic hydrocarbon (such as benzyl, naphthyl, anthracyl, etc.) and heterocyclic (such as furanyl, thiophenyl, pyridyl, etc.) substituents; and "aralkyl" refers to benzyl, alkylphenyl, alkylnaphthyl, etc. By "optionally substituted" herein is meant that the subject alkyl, aryl or aralkyl group may bear one or more substituents which are the same or different and are substantially inert to an addition or nucleophilic substitution reaction with the hydroxyl, thiol or primary or secondary amino groups of the compounds of biological interest to be recovered by affinity chromatographic methods using the product of Formula I(a) or I(b) under the specified chromatography conditions. In general, undesired side-reactions with the molecules to be recovered are likely to occur only with highly reactive disulfide or thiol groups and halogens (generally, as are found in structures where there are substantial electronic and/or steric factors contributing to reactivity) or "activated" hydroxyl groups (for example, FMP-treated hydroxyl groups as taught in U.S. Pat. No. 4,582,875). Accordingly, suitable substituents for the subject alkyl, aryl or aralkyl groups include hydroxyl and hydroxylalkyl; primary, secondary or tertiary amino and alkylamino; sulfonyl and alkylsulfonyl; carboxyl and carboxylate; alkylcarbonyl; acyl and carboxyalkyl; nitro and nitroalkyl; amido and alkylamido; and thioalkyl.

The compounds of this aspect of the invention, the structures of which are believed to be represented by one of the general formulas I(a) or I(b), may be prepared by a number of different synthetic routes. According to a first such route, as described in several examples in the specification of Ser. No. 07/243,352, a suitable polymeric carrier is reacted with a halogen-substituted pyridine and a pyridine base, such as 4-dimethylaminopyridine (DMAP). In an alternative route of synthesis, the halogen-substituted pyridine is first reacted with the pyridine base to form an intermediate, some of which are themselves novel compounds, and the intermediate in turn is reacted with the polymeric carrier to provide the compounds of the invention.

It was initially believed that in all of the synthetic reaction schemes proposed in Ser. No. 07/243,352 the base was involved solely in promoting activation of suitable nucleophilic groups on the polymeric carrier by reaction with a suitable 2-halopyridine. Thus, the particular tertiary base employed in the activation reaction was believed to be irrelevant, because it was viewed to serve essentially a catalytic role. In fact, it is suggested in Ser. No. 07/243,352 simply that activation of the nucleophile containing polymeric carrier be carried out in the presence of a "slight excess of a tertiary amine, such as triethylamine, tributylamine or 4-dimethylaminopyridine . . . "

It has now been determined that, in contrast to the type of activation which occurs in the presence of other bases and/or with halogen-substituted pyridine reactants outside the classes hereinafter specified, an entirely different reaction mechanism appears to be involved in the reaction of a nucleophile containing polymeric carrier with a pyridine base and a halogen-substituted pyridine pursuant to this aspect of the present invention. Indeed, when the reactants are chosen in accordance with this aspect of the present invention, it is believed that both the pyridine base and the halogen-substituted pyridine are incorporated into the final product. Moreover, it is further believed that the proposed structure of general formula I(a) may be formed by an opening of the pyridine base ring during the course of the synthesis of the compounds of this aspect of the instant invention, resulting in the formation of an extended conjugated system. Such an extended conjugated system is also present in alternative proposed structure I(b). As a consequence, the novel compounds of this aspect of the present invention are found to be strongly fluorescent, whereas neither the individual reactants nor the products of an activation/coupling reaction scheme (as contemplated in Ser. No. 07/243,3520) exhibit in general any such fluorescence.

While it has not yet been determined with certainty the actual mechanism whereby the compounds of the invention are formed, and indeed whether the compounds of the invention do in fact have the structure proposed in general formula I(a) or I(b), it is believed that formation of this aspect of the compounds of the present invention proceeds in accordance with a reaction pathway as illustrated in FIG. 1. This proposed reaction pathway has been derived with respect to general formula I(a) in accordance with the study of Chambers et al. as to the mechanisms involved in the reaction of pentachloropyridine with an excess of pyridine at 50° C. to form a monopyridinium salt, followed by ring opening of the salt with an excess of dimethylamine in water at room temperature [Chambers, R. D. et al, "Pyridinium salts of halogenated heterocyclic compounds," Chem. Ind. (London) 89 (1975)].

The halogen-substituted pyridines which can be used in the preparation of the chromatographic adsorbents of this aspect of the present invention from suitable polymeric carriers comprise a class of pyridine compounds defined differently from the 2-halopyridines contemplated for use in activation of nucleophile-containing polymers pursuant to Ser. No. 07/243,352. For purposes of activation and coupling pursuant to the methods of Ser. No. 07/243,352, any 2-halopyridine may be employed in which at least one of the ring positions of the 2-halopyridine is substituted with an electron withdrawing group. Pursuant to this aspect of the present invention, however, there is required a halogen-substituted pyridine represented by means of the general formula II:

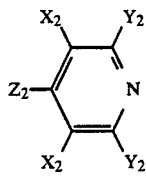

wherein
 each $X_2$ is independently selected from the group consisting of halogen, trihalomethyl and nitro;
 at least one $Y_2$ is halogen and the other $Y_2$ is selected from the group consisting of halogen and $-A_1R_4$, in which $A_1$ is O, S or $NR_5$, $R_4$ is optionally substituted alkyl, aryl, or aralkyl, and $R_5$ is optionally substituted alkyl, aryl or aralkyl; and
 $Z_2$ is a suitable leaving group (generally, halogen such as F or Cl).

Typical halogen-substituted pyridine compounds for use in accordance with this aspect of the present invention include pentafluoropyridine(PFP),3,5-dichloro-2,4,6-trifluoropyridine (DCTFP), and pentachloropyridine (PCP).

As disclosed in Ser. No. 07/243,352, the polymeric carrier can be a water insoluble or water soluble polymeric substance. Except as indicated below, the choice of the carrier is not critical for carrying out the process of the present invention. In principle, any type of carrier can be used which has a polymeric nature and contains at least one nucleophilic group such as a hydroxyl, amino or sulfhydryl group bonded to a carbon atom which is available for activation and coupling. The carrier is chosen with regard to the requirements in the individual situation. The carrier may be comprised of natural, semi-synthetic or synthetic polymeric materials containing nucleophilic groups. Examples of important natural and semi-synthetic carrier materials are polysaccharide containing materials, for example, cellulose, agarose, dextran and cross-linked products thereof. Examples of synthetic carriers are poly(ethylene glycol), poly(vinyl alcohol), poly(hydroxyethyl methacrylate), nylon and the like. It is, of course, also possible to use carriers such as inorganic supports which do not normally contain hydroxyl groups but which, by suitable treatment, can be provided with such groups. An example is silica particles, to the surface of which have been bonded groups containing at least one nucleophilic group. Carriers may be used in the form of various solids, such as gels, beads, fibers, fabrics or membranes or in the form of a soluble polymer.

Whereas the activation of nucleophile-containing polymeric carriers pursuant to the methods of Ser. No. 07/243,352 is carried out in the presence of a slight excess of any tertiary amine exhibiting the desired basic activity (such as triethylamine, tributylamine or 4-dimethylamino-pyridine) in a polar organic solvent such as acetone, dimethylformamide (DMF), acetonitrile or tetrahydrofuran (THF), pursuant to this aspect of the present invention the pyridine base is itself a reactant involved in the formation of the novel chromatographic adsorbents and is incorporated into the structure of the proposed final product. Generally, the pyridine base for use in the formation of the products of this aspect of the invention is of the general formula III:

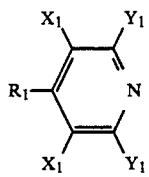

wherein
 each $X_1$ is hydrogen or optionally substituted alkyl, aryl or aralkyl;
 at least one $Y_1$ is hydrogen and the other is hydrogen or optionally substituted alkyl, aryl or aralkyl; and
 $R_1$ is hydrogen, optionally-substituted alkyl, aryl or aralkyl, or $-NR_2R_3$, in which $R_2$ and $R_3$ are the same or different and are optionally-substituted alkyl, aryl or aralkyl.

Pursuant to a first synthetic route as described in Ser. No. 07/243,352 (and presumed at the time to result in an activation of the nucleophile on the polymeric carrier), the pyridine base, the polymeric carrier and the halogen-substituted pyridine are reacted together in a so-called one pot reaction in a suitable organic solvent, preferably a polar organic solvent. A wide range of temperature and pressure conditions are suitable. In general, the reaction may be carried out at a temperature of about 0° to about 90°, preferably at an ambient temperature on the order of about 22° to 35° C., over a time period of about 0.1 to about 20 hours, preferably about 0.1 to about 2 hours, at atmospheric or slightly elevated pressure. Suitable solvents include dimethylformamide (DMF), acetonitrile and tetrahydrofuran (THF). The resulting products are believed to have a structure as represented by general formula IV(a) or IV(b):

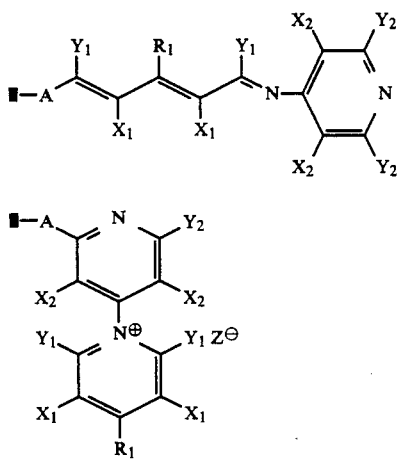

wherein the substituents are as previously defined. These compounds (depending upon the substitution pattern) are either effective as chromatographic adsorbents per se and/or serve as precursors to such adsorbents (e.g., upon further reaction with a suitable base or low molecular weight compounds, such as suggested in Ser. No. 07/243,352).

Pursuant to an alternative synthetic route, the compounds of general formulas II and III are first coupled together under reaction conditions similar to those described above for the one-pot reaction and in a suitable organic solvent to form an intermediate of general formula V:

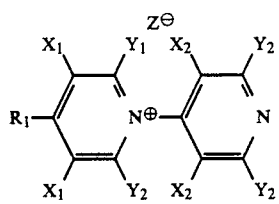

wherein Z is a suitable counterion (for example, halogen) and the remaining substituents are as previously defined. In this case, a particularly suitable solvent is chloroform, as the intermediate will in general precipitate out of solution. This intermediate in turn is then reacted in a suitable organic solvent under basic conditions (i.e., in DMF in the presence of tributylamine) with the polymeric carrier to form a compound of general formula IV(a) or IV(b). This reaction may also be carried out over a fairly broad range of temperatures and times (e.g., a temperature of about 0° to about 90°, preferably at an ambient temperature on the order of about 22° to 35° C., over a time period of about 0.1 to about 20 hours, preferably about 0.1 to about 2 hours, at atmospheric or slightly elevated pressure).

As indicated in Ser. No 07/243,352, the resultant products were found to be stable for at least four months when stored at 4° C. in acetone. Depending upon the nature of the particular substituents involved, the chromatographic adsorbents of the invention can also be stored in dilute mineral acids such as 2 mM phosphoric acid, or in dry form, if desired.

In accordance with this aspect of the present invention, the reaction product of general formula IV(a) or IV(b), i.e., the reaction product of the polymeric carrier with an appropriate halogen-substituted pyridine and pyridine base, may in turn be reacted with a base or a low molecular weight nucleophilic compound, in particular in those cases where at least one $Y_2$ in Formula IV(a) or $Y_2$ in Formula IV(b) is halogen. Thus, it is contemplated according to this aspect of the present invention to replace a given $Y_2$ substituent which itself may or may not fall within the definition of Y with a different substituent also falling within the definition of Y, so as to provide a final product having a different (e.g., selective or enhanced) binding affinity for a given material or group thereof. Preparation of the desired product may be indicated by the presence of fluorescence in the recovered gel in aqueous and/or other polar solvent solution.

Suitable low molecular weight compounds for preparation of the desired chromatographic adsorbents are of the general formula VI:

$$R_6-B-R_7$$

wherein B is an optionally-substituted alkyl, aryl or aralkyl moiety of 2 to about 10 carbon atoms; and each of $R_6$ and $R_7$ is —OH, —SH or —$NR_8R_9$, in which each of $R_8$ and $R_9$ is hydrogen or optionally-substituted alkyl, aryl or aralkyl. Examples of suitable low-molecular-weight compounds include 2-mercaptoethanol, ethylene glycol, and ethanolamine as suggested in Ser. No. 07/243,352 of the type of ligand which can be used to form gels which bind proteins and other organic molecules of interest non-covalently. Other suitable low molecular weight compounds include non-vicinal diols and glycols, alkylenediamines, dithiothreitol and amino acids, such as glycine.

Reacting an intermediate of general formula IV wherein $Y_2$ is, e.g., halogen with hydroxide ions, such as by treatment with a base (for example, NaOH, NaHCO$_3$ or Na$_2$CO$_3$) also produces gels which can be used to bind reversibly various biologically active materials non-covalently.

Reaction of the low molecular weight molecules with the intermediate of general formula IV can be accomplished under varying conditions of temperature and pH and can be performed in aqueous reaction media as well as in organic solvents. In general, any solvent which is inert to the reactants (i.e., any non-nucleophilic solvent) may be employed. Temperatures on the order of about 0° to about 100° C. and times of about 10 minutes to about 20 hours are generally suitable. Reaction conditions are not critical and are primarily chosen with regard to the sensitivity of the reactant and to practical considerations of convenience. Mild reaction conditions are preferred. It is, for example, often suitable to work at ambient temperatures and pressures. The pH at which the reactions are carried out can range from an acidic pH, for example, a pH less than about 4, to an alkaline pH, for example, a pH of about 10.

The chromatographic adsorbents prepared in accordance with this aspect of the present invention are characterized by a very stable chemical linkage between the affinity ligand and the solid matrix to which it is bound. If such stable chemical linkage is not formed, loss of the affinity ligand from the matrix could result in contamination of the purified material obtained by use of such chromatographic matrix and shortening of the useful life of the matrix. The described reaction schemes result in a minimal probability of detachment of affinity ligands even upon subsequent exposure to basic and nucleophilic buffers, and thus provides superior chromatographic adsorbents.

Another advantage is believed to be the realization of significantly greater affinity binding capacity of the chromatographic adsorbent than is the case with many other heretofore known adsorbents, including the preferred proteinaceous adsorbents in current use such as bound Protein A gels. A primary advantage of the inventive compounds, of course, is that highly efficient and selective binding of organic molecules of interest, in particular proteins, may be achieved using a synthetic affinity ligand of relatively low molecular weight (on the order of less than about 1000), rather than a proteinaceous ligand as heretofore preferred, such as Protein A (molecular weight 42,000).

The novel gels of this aspect of the present invention are particularly useful for non-covalent binding of biologically active ligands, for example, proteins, enzymes, antibodies, antigens, amino acids, nucleic acids, thiol compounds, cofactors, haptens and many other types of biologically active ligands. Of particular interest is the extraordinary affinity of the reaction product of either Sepharose Cl-4B or Fractogel TSK HW 75 F activated by 3,5-dichloro-2,4,6-trifluoropyridine and 4-dimethylaminopyridine with ethylene glycol (the "O-gel") for IgG from a variety of different species, including rats, goats and chickens (for which Protein A does not show significant affinity). Such binding can be achieved under relatively low salt conditions such as 0.02M sodium phosphate (pH 7.5), 0.15M NaCl in 0.02M to 0.05M sodium phosphate (pH 7.4) or 0.05M sodium bicarbonate (pH 8.5). These gels can also be used for the enrichment of the specific radioactivity of labeled proteins, for example I-125 labeled bovine serum albumin (BSA) or human IgG.

Based on detailed analysis of results using an exemplary compound in accordance with the instant invention (i.e., the aforementioned O-gel) for the recovery of particular proteins from diluted serum samples obtained from various species, it has been determined that the gels of the present invention possess several unique attributes which distinguish them from all known chromatographic adsorbents, and in particular from the thiophilic gels of Porath et al. First, the binding of proteins to O-gel does not require the presence of a high concentration of water-structure-forming salts, as is the case with the thiophilic gels. In fact, almost all the serum proteins applied to the O-gel in the absence of high salt concentrations were adsorbed, and some albumin from the serum was actually desorbed by the presence of high salt. In this respect, the chromatographic adsorbent of the instant invention may also be distinguished from bound Protein A gels, with respect to which there is an increase in binding observed using elevated concentrations of a buffer comprising a monovalent cation and a polyvalent anion over a specified pH range (as disclosed in U.S. Pat. No. 4,801,687), and allegedly observed using high concentrations of any inorganic salt at a pH above 7.5 (cf. U.S. Pat. No. 4,704,366).

Further, the desorption of bound IgG from O-gel is achieved by decreasing the pH of the eluting solution. According to the method of Porath et al., desorption is achieved through decreases in salt concentration. Perhaps as a consequence of this difference, the albumin fraction recovered using O-gel is highly pure and almost entirely free of other protein contaminants, in contrast to product as recovered using the thiophilic gel.

Finally, the chemistry of the non-covalent binding according to the present invention is clearly different from that of the thiophilic gels. Thiophilic gels require the presence of sulfone and thioether functional groups for binding. In contrast, there is no participation of any sulfur element in the O-gels; moreover, even in those gels wherein sulfur-containing ligands are employed, the nature of the interaction between the affinity ligand and the molecule bound thereto is clearly different in nature from what occurs in the case of thiophilic gels.

The details of the mechanism of protein adsorption to the compounds of the present invention, such as O-gel, are currently not known. The unique adsorption characteristics of the O-gel and its analogues, however, may be associated with the formation of a highly conjugated system, as evidenced by the strong fluorescence of O-gel in aqueous solution. In any event, the high capacity for adsorption of proteins at low ionic strength and the high binding selectivity of the gel are both contrary to commonly known, non-selective processes of hydrophobic interaction chromatography. Moreover, continuous adsorption of proteins at 0.5M salt concentrations is not consistent with ion-exchange chromatography. The absence of any sulfur-containing group in O-gel clearly disqualifies the process as thiophilic. Thus, based on the available information, it appears that the adsorption of proteins and other organic molecules of biological interest to compounds of the instant invention, such as O-gel, involves a novel protein adsorption process heretofore neither demonstrated nor recognized.

The invention will be better understood by reference to the following examples which are intended for purposes of illustration and are not to be construed as in any way limiting the scope of the present invention, which is defined in the claims appended hereto.

Examples 1-14 illustrate exemplary methods for use in preparation of novel chromatography adsorbents in accordance with aspects of the present invention. Examples 15-28 illustrate the use of the novel gels in separation and purification of materials of biological interest. Examples 29-38 illustrate additional methods for the preparation and use of activated polymeric carriers and derivatives thereof in accordance with further aspects of the present invention.

EXAMPLE 1

Preparation of Reaction Product of Sepharose CL-4B with 4-Dimethylaminopyridine (DMAP) and 3,5-Dichloro-2,4,6-trifluoropyridine (DCTFP)

Sepharose CL-4B, a cross-linked agarose gel from Pharmacia Fine Chemicals, Uppsala, Sweden (100 ml) was washed five times with 100 ml distilled water each time. The washed gel was suspended in 100 ml distilled water in a 2 L beaker mounted on a shaker rotating at 100 rpm. To the gel suspension was added 1 L acetone over 30 minutes duration. The gel was filtered and resuspended in 1 L dry acetone and was tumbled at room temperature for 15 minutes after filtering. The gel was then suspended in 200 ml dry acetone.

To 10 ml acetone washed gel, in a polypropylene bottle was added 30 ml dry DMF. The suspension was tumbled for 5 minutes. After filtering, the gel was suspended in 10 ml dry DMF containing 5.5 millimoles DMAP. To the gel suspension was further added 25 ml DMF containing 5 millimoles of DCTFP. After tumbling at room temperature for 2 hours, the gel was washed with 100 ml DMF and twice with 100 ml acetone each time. The washed gel was stored in 30 ml acetone at 4° C.; under these conditions, it can remain stable for several weeks.

EXAMPLE 2

Preparation of Reaction Product of Sepharose CL-4B with DMAP and Pentachloropyridine (PCP) or Pentafluoropyridine (PFP)

The procedure of Example 1 was repeated with the following halogen-substituted pyridines: pentafluoropyridine (PFP) and pentachloropyridine (PCP).

EXAMPLE 3

Coupling of Dithiothreitol (DTT) to Reaction Product of DCTFP, DMAP and Sepharose CL-4B The reaction product of Example 1 (2 ml) was washed with 20 ml distilled water. The washed gel was suspended in 15 ml 0.1M DTT in 0.05M sodium bicarbonate, pH 8.5 and mixed vigorously on a Vortex mixer briefly. The gel suspension was left standing at room temperature for 48 hours. The reacted gel was washed with 20 ml of distilled water, 1M NaCl, 8M urea, distilled water and 0.1M sodium bicarbonate, pH 8.5. The density of thiol group was determined by using Ellman reagent [Ellman, G. L., Arch. Biochem. Biophys. 82, 70 (1959)] and was found to be 42–48 micromoles per milliliter of gel.

EXAMPLE 4

Preparation of Reaction Product of Paper with DMAP and DCTFP in Dimethylformamide (DMF)

Twenty pieces of Schleicher & Schuell 589 WH filter paper (5 cm×6.5 cm) were immersed in 100 ml dry DMF for 10 minutes. The papers were removed and placed in 100 ml dry DMF containing 10 millimoles DMAP. The paper suspension was placed on a shaker rotating at 100 rpm for 5 minutes at room temperature. To this suspension was added 10 millimoles DCTFP in 100 ml dry DMF and the shaking was continued. At various time intervals (0.5, 5, 10, 15, 30, 60, 90 minutes), one piece of the paper was removed, blotted dry on several layers of paper towel, placed in 100 ml dry DMF and shaken for 5 minutes. This washing step was repeated once more with dry acetone instead of dry DMF. Finally the paper was air-dried in a fume hood.

EXAMPLE 5

Preparation of Reaction Product of Nylon Membrane with DMAP and DCTFP

Ten Nylon membrane disks (MicronSep Magna Nylon 66 Type 5 from Fisher Scientific Co.) wera suspended in 25 ml DMF containing 13.75 millimoles DMAP. To this suspension was added 62.5 ml DMF containing 12.5 millimoles DCTFP. The membrane suspension was rotated at 150 rpm. at room temperature for 2 hours. Then the membranes were washed successively with 200 ml DMF and 200 ml acetone. The washed membranes were air dried at room temperature and stored dessicated at 4° C.

EXAMPLE 6

Preparation of 2-Mercaptoethanol/DCTFP Substituted Gel

The reaction product of Example 1 (10 ml) was washed with 100 ml distilled water and 100 ml 0.1M sodium bicarbonate, pH 9. The washed gel was suspended in 10% 2-mercaptoethanol in 0.1M sodium bicarbonate, pH 9 and tumbled end-to-end at room temperature for 24 hours. The gel was washed with 100 ml bicarbonate buffer and then resuspended in 20 ml 0.1M NaOH and tumbled at room temperature for 14 hours. Finally, the gel was washed sequentially with 100 ml 1M NaCl, 100 ml distilled water and 100 ml PBS; the product was stored in PBS at 4° C.

In the same manner, an affinity gel was prepared using ethanolamine or 3-mercaptopropionic acid in place of the 2-mercaptoethanol.

EXAMPLE 7

Preparation of Ethylene Glycol Substituted Gel (O-Gel)

The procedure of Example 6 was followed, using 1 ml ethylene glycol in place of the 2-mercaptoethanol. After resuspension of the product in 20 ml 0.1M NaOH and tumbling at room temperature for 14 hours, the product was washed sequentially with 100 ml distilled water, 100 ml 1M NaCl, 100 ml distilled water and 100 ml PBS. The product was stored in PBS at 4° C. when not in use.

EXAMPLE 8

Preparation of 2-Mercaptoethanol/PFP Substituted Gel

The procedure of Example 7 was repeated using the reaction product of PFP, DMAP and Sepharose CL-4B. In place of 2-mercaptoethanol, ethylene diamine, 3-mercaptopropionate, ethylene glycol and ethanolamine were also introduced into the final product following analogous procedures.

EXAMPLE 9

Preparation of Hydroxide Ion Treated Gels

The procedure of Examples 6 and 8 was repeated except that the respective reaction products were suspended in 0.1M sodium bicarbonate, pH 9 without addition of an organic ligand.

EXAMPLE 10

Preparation of Iodoacetamide-Blocked Dithiothreitol Substituted Gel

The reaction product of Example 3 was washed with distilled water and then suspended in 0.1M iodoacetamide (0.1M phosphate buffer, pH 7.0) for 14 hours at room temperature. The gel was washed with distilled water and 0.5M NaCl solution and stored at 4° C. in PBS.

EXAMPLE 11

Preparation of Glycine Substituted Gel

The reaction product of Example 1 (10 ml) was washed with 100 ml distilled water and 100 ml 0.1M sodium bicarbonate (pH 9). The washed gel was suspended in 1M glycine (0.1M sodium bicarbonate, pH 9) and tumbled end-to-end for 24 hours at room temperature. The gel was washed with 100 ml bicarbonate buffer and then resuspended in 20 ml 0.1M NaOH. This suspension was tumbled for 14 hours at room temperature. Finally, the gel was washed with 100 ml 1M NaCl, 100 ml distilled water and 100 ml PBS. The product was stored at 4° C. in PBS.

EXAMPLE 12

Preparation of Glutamate and Ethylene Diamine Substituted Gels

The reaction product of Example 1 (10 ml) or of Example 2 (10 ml) was washed with 100 ml distilled water and 100 ml 0.1M sodium bicarbonate (pH 9). The washed gel was suspended in 1M glutamate (0.1M sodium bicarbonate, pH 9) and tumbled end-to-end for 24 hours at room temperature. The gel was washed with 100 ml bicarbonate buffer and then resuspended in 20 ml 0.1M NaOH. This suspension was tumbled for 14 hours at room temperature. Finally, the gel was washed with 100 ml 1M NaCl, 100 ml distilled water and 100 ml PBS. The product was stored at 4° C. in PBS.

Following an analogous procedure using 1M ethylene diamine, the ethylene diamine substituted gel was also prepared.

EXAMPLE 13

Preparation of Adduct of DMAP and DCTFP (Intermediate)

One equivalent each of 4-dimethylaminopyridine (DMAP) and 3,5-dichloro-2,4,6-trifluoropyridine (DCTFP) dissolved in chloroform were reacted together at room temperature for about 14 hours and then at −20° C. for about 6 hours. Precipitated solids were removed and washed three times with diethyl ether. The product was recrystallized from tetrahydrofuran. The overall yield was approximately 70%.

EXAMPLE 14

Preparation of Ethylene Glycol Substituted Gel via Reaction Product of DMAP-DCTFP Adduct with Sepharose CL-4B Sepharose CL-4B (25 ml) was washed with acetone to remove water. The washed gel was then suspended in 25 ml DMF containing 55 mmoles tributylamine and 50 mmoles of the adduct of Example 13. The suspension was tumbled end-to-end for about 2 hours at room temperature. The product was washed with 250 ml DMF and then twice with 250 ml acetone per wash. The product gel was stored in acetone. To demonstrate the activation of the gel, covalent binding of a serum protein was attempted; it was determined that the gel was able to bind covalently 15 mg bovine serum albumin per ml gel.

The activated gel (20 ml) was washed with 100 ml distilled water, then with 100 ml 0.1M NaHCO$_3$ (pH 9). The washed gel was suspended in 100 ml 0.1M NaHCO$_3$ (pH 9) containing 10% ethylene glycol. The suspension was tumbled end-over-end at room temperature for 24 hours. The gel was resuspended in 0.1M NaOH and tumbled for 14–20 hours at room temperature. Finally, the gel was washed sequentially with 100 ml each of distilled water, 1M NaCl, distilled water and PBS.

EXAMPLE 15

Non-covalent Binding of Serum Proteins

The gels of Examples 6–12 (0.5–1.0 ml) were mixed with 1–2 ml protein solution (20–40 mg protein/ml) in a test tube and tumbled end-to-end at room temperature for 5 minutes. After centrifugation, the supernatant was removed and the gel was washed twice with PBS. The amount of protein in the supernatant and washes was determined and was equated to the amount unbound. In some cases, additional washing steps were introduced. The results are shown in Table I.

TABLE I

| Halopyridine Reactant | Ligand | Serum Protein Bound (mg protein per ml gel) | | |
|---|---|---|---|---|
| | | Bovine Serum[a] albumin | Human Serum[a] albumin | Human IgG[b] |
| DCTFP | Ethylene glycol | 39.6 | 51.0 | 20.3 |
| DCTFP | 2-Mercaptoethanol | 22.0 | — | 18.6 |
| DCTFP | Ethanolamine | 42.2 | 52.0 | — |
| DCTFP | Hydroxide (NaOH treated) | 33.6 | 51.8 | — |
| DCTFP | Glutamate | — | 7.4 | — |
| DCTFP | Glycine | — | 33.4 | — |
| DCTFP | Mercaptopropionate | — | 3.2 | — |
| DCTFP | Dithiothreitol | — | 25.7 | — |
| DCTFP | Dithiothreitol-iodoacetamide | — | 29.2 | — |
| DCTFP | Ethylene Diamine | — | 42.2 | — |
| PFP | Ethylene glycol | 37.8 | 45.0 | — |
| PFP | 2-Mercaptoethanol | 34.4 | — | — |
| PFP | Ethanolamine | 40.4 | 48.0 | — |
| PFP | Hydroxide (NaOH treated) | 33.5 | 51.6 | — |
| PFP | Mercaptopropionate | — | 42.3 | — |

TABLE I-continued

| Halopyridine Reactant | Ligand | Serum Protein Bound (mg protein per ml gel) | | |
|---|---|---|---|---|
| | | Bovine Serum[a] albumin | Human Serum[a] albumin | Human IgG[b] |
| PFP | Glycine | — | 41.8 | — |

[a]Bovine serum albumin and human serum albumin were dissolved in 0.05 M sodium bicarbonate, pH 8.5
[b]Human serum IgG was dissolved in PBS.

EXAMPLE 16
Enrichment of Specific Radioactivity of I-125 Labeled Bovine Serum Albumin (BSA) by Selective Adsorption on 2-Mercaptoethanol Substituted Gel A quantity of 4 ml I-125 labeled BSA having a specific activity of 1000 cpm per mg protein in a concentration of 20 mg/ml was added to 0.5 ml of the product of Example 7 at room temperature for 5 minutes. Then the gel was centrifuged briefly and the supernatant was removed. The gel was washed 3 times with 20 mM sodium phosphate, pH 7.5 before the I-125 labeled BSA was eluted with two 4 ml portions of 0.1M glycine-HCl, pH 2.8. The specific activity of the I-125 labeled BSA was enriched to 3550 cpm per mg protein.

EXAMPLE 17
Enrichment of Specific Radioactivity of I-125 Labelled Human Immunoglobulin (IgG) by Selective Adsorption on Ethylene Glycol Substituted Gel The procedure of Examples 15 and 16 was followed using I-125 labeled human IgG having a specific activity of 5,100 cpm per mg protein in a concentration of 20 mg/ml. The specific activity was enriched to 12,200 cpm per mg protein.

EXAMPLE 18
Separation of IgG and Serum Albumin from Human Serum by Chromatography on O-Gel 3 ml of the gel prepared in accordance with Example 8 was washed with about 10 ml of 20 mM sodium phosphate, pH 7.4. 1 ml filtered human serum (diluted 1:100 in 20 mM phosphate buffer, pH 7.4) was passed through the column at room temperature at a flow rate of 1.25 ml per minute. The column was then washed with the same phosphate buffer.

Bound proteins were eluted, first with 10 mM sodium phosphate containing 0.5M $K_2SO_4$ (pH 7.4), followed by 0.1M glycine buffer at progressively lower pH values of 5.0, 4.0 and 2.8, all at the same flow rate previously indicated. Except for a first fraction comprising non-adsorbed proteins and having a volume of 60 ml, 1.5 ml fractions were collected for each wash and the OD at 280 nm for each fraction monitored continuously in a LKB 2238 UV Cord. Fractions were collected in an LKB 2070 Ultrorac fraction collector. The pH was monitored using an LKB 2195 pH/Ion Monitor.

As illustrated in FIG. 2, the diluted human serum gave a chromatogram with five protein fractions. Peak I contained any non-adsorbed proteins; based on absorbance at 280 nm, the unbound protein represented 8% of the total protein applied to the column. Peak II contained materials desorbed by 10 mM phosphate buffer, pH 7.4, containing 0.5M $K_2SO_4$. This fraction contained most of the serum albumin, and accounted for 32% of the total protein. Peak III material was desorbed with 0.1M glycine at pH 5.0; peak IV material, at pH 4.0; and peak V material, at pH 2.8. The peak III fraction contained most of the immunoglobulin G (with very minor amounts of contaminating serum albumin); the fraction accounted for 15% of the total protein applied. Immunoglobulins M and A were found in the fractions of peaks IV and V, respectively.

Figure 3:
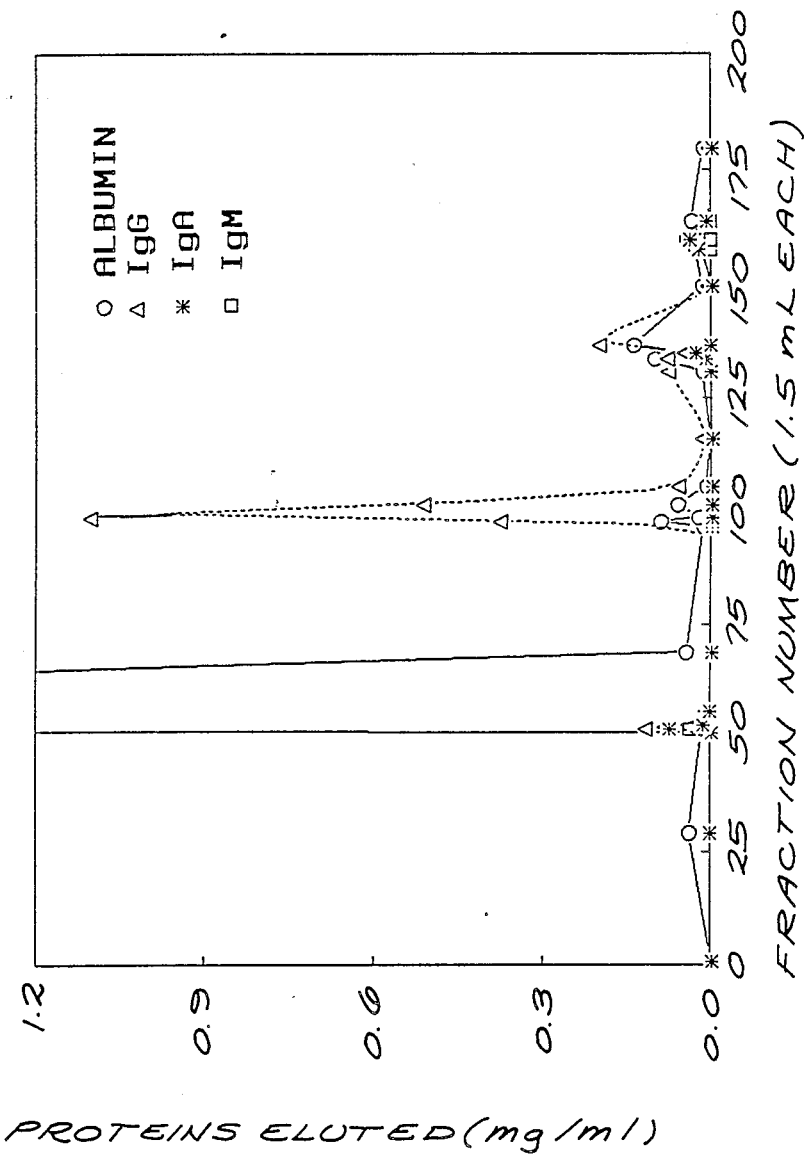
FIG. 3 illustrates specific sandwich ELISA patterns of human serum after chromatography on O-gel.

The concentrations of serum albumin and various immunoglobulins in each fraction was determined using specific Sandwich ELISA. FIG. 3 illustrates the specific sandwich ELISA patterns of the serum after chromatography under the conditions specified for FIG. 2. The legends identify the protein for which each ELISA is specific.

Figure 4:
FIG. 4 illustrates the results of SDS-gradient polyacrylamide gel electrophoresis on fractions of human serum recovered by elution from an O-gel column.

The identity of the various proteins was further confirmed by 10–15% gradient SDS polyacrylamide gel electrophoresis (PAGE) under reducing conditions. The developed gel as depicted in FIG. 4 comprises 7 lanes: lane 1, for molecular weight marker reference proteins; lane 2, for unfractionated human serum; and lanes 3–7, for fractions I–V of FIG. 2, respectively.

Figure 6A:
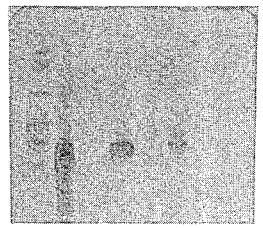
FIG. 6 illustrates SDS-gradient polyacrylamide gel electrophoresis of mouse (A) and rabbit (B) sera.
Figure 6B:
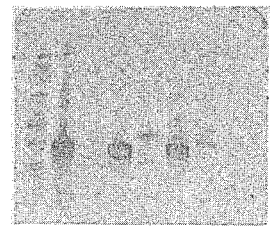
Figure 5A:
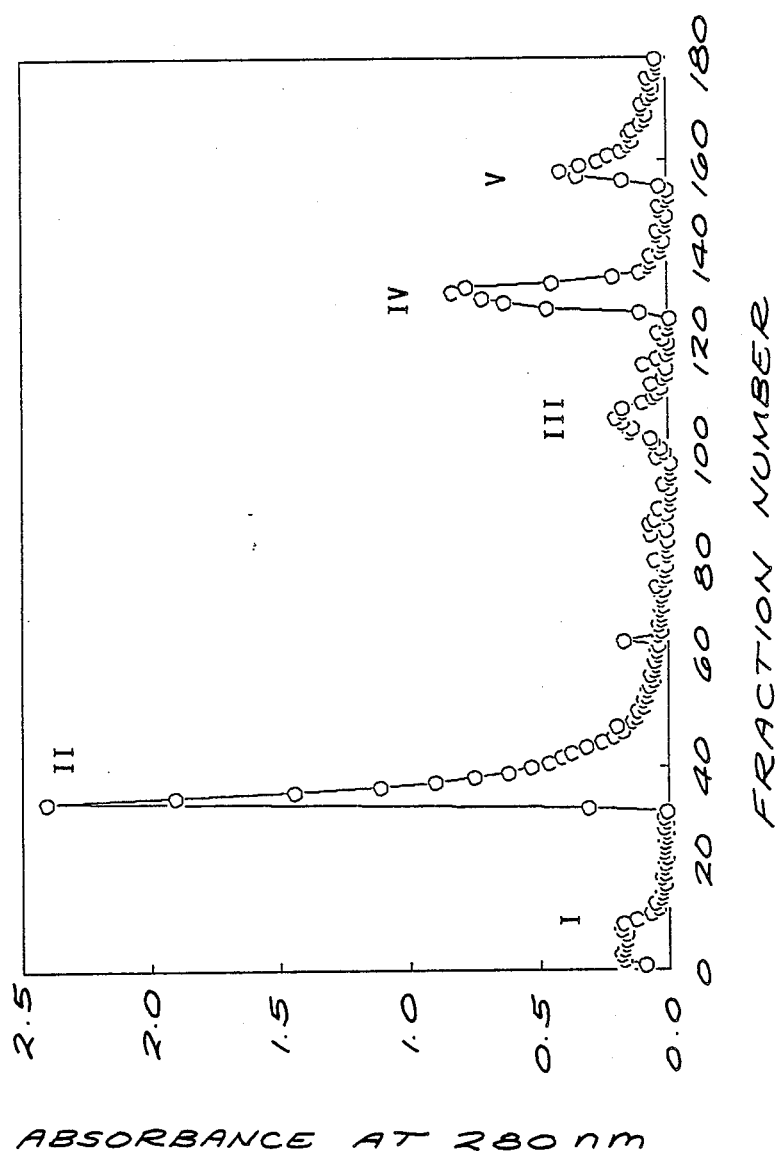
FIG. 5 illustrates the elution pattern of mouse serum (A) and rabbit serum (B) obtained by chromatography on O-gel.
Figure 5B:
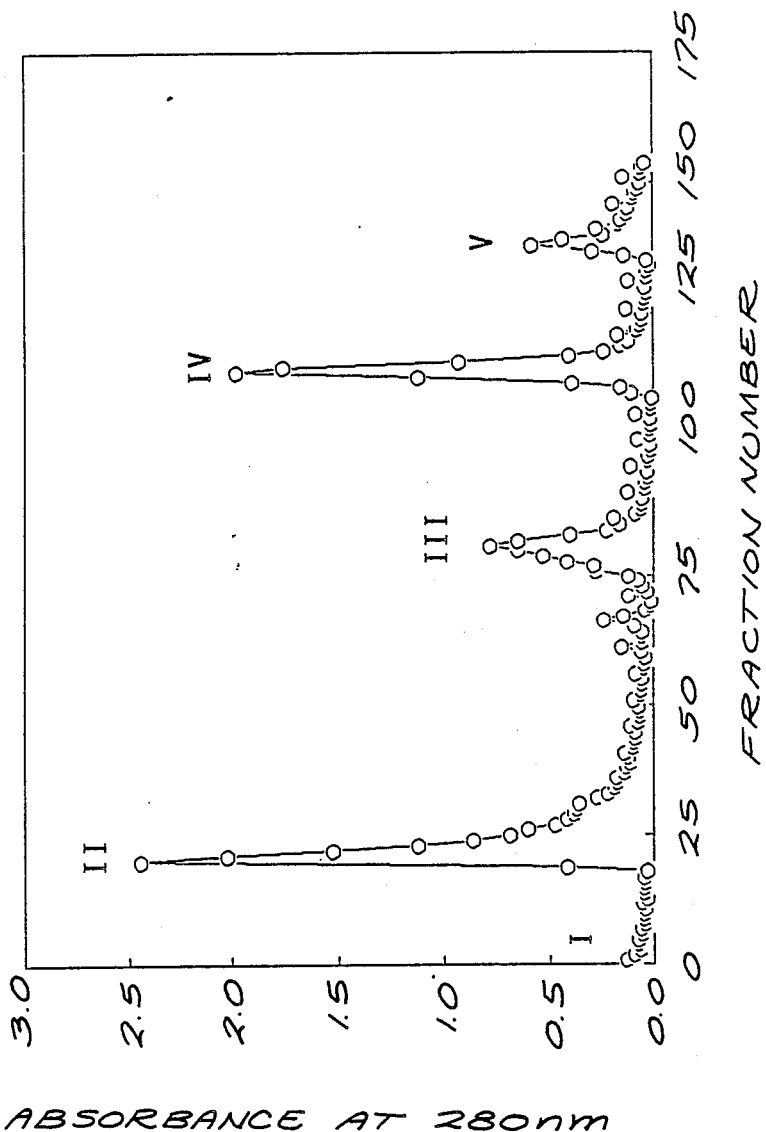

Similar chromatographic patterns were observed for rabbit and mouse sera (FIGS. 5A and 5B, respectively). Identification of the major proteins in each peak fraction of the rabbit and mouse sera by PAGE (FIGS. 6A and 6B, respectively) was also consistent with the separation observed with human sera.

In addition, similar chromatographic patterns were observed when the 0.5M $K_2SO_4$ wash solution was replaced with phosphate buffer saline (PBS). In the latter instance, however, the level of albumin contamination in the IgG fraction was higher.

The chromatograms of human, rabbit and mouse sera, as well as the immunological and electrophoretic analyses of peak protein fractions, all illustrate the extraordinary selectivity and protein biding capacity of the gel for serum albumin and for various immunoglobulins. It is particularly worth noting that none of the commercially available immobilized Staphylococcus Protein A gels bind IgG from rat sera; however, the inventive gel has been shown to be as effective with rat sera as with that of other species tested.

EXAMPLE 19
Separation of Bovine Serum Albumin and IgG

Figure 7:
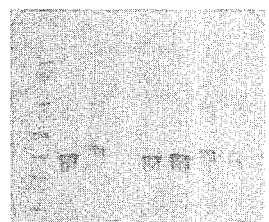
FIG. 7 illustrates SDS-gradient polyacrylamide gel electrophoresis of fractions recovered by O-gel chromatography of a mixture of bovine serum albumin and IgG.

Fifteen ml solution containing a mixture of 7.5 mg bovine serum albumin and 7.5 mg bovine immunoglobulin G in 20 mM sodium phosphate buffer, pH 7.5 was applied on a column of O-gel (1 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 7, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl ( containing albumin); and columns (7) and (8) are fractions eluted with 0.1M glycine, pH 4 (containing IgG).

EXAMPLE 20

Separation of Chicken Serum Albumin and IgG

Figure 8:
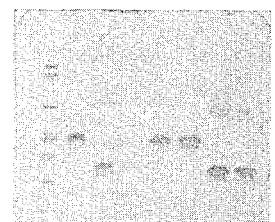
FIG. 8 illustrates SDS-gradient polyacrylamide gel electrophoresis of fractions recovered by O-gel chromatography of a mixture of chicken serum albumin and IgG.

Fifteen ml solution containing a mixture of 7.5 mg chicken serum albumin and 7.5 mg chicken immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 8, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH 4 (containing IgG).

EXAMPLE 21

Separation of Goat Serum Albumin and IgG

Figure 9:
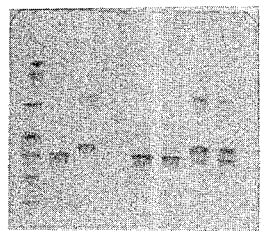
FIG. 9 illustrates SDS-gradient polyacrylamide gel electrophoresis of fractions recovered by O-gel chromatography of a mixture of goat serum albumin and IgG.

Fifteen ml solution containing a mixture of 7.5 mg goat serum albumin and 7.5 mg goat immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 9, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH 4 (containing IgG).

EXAMPLE 22

Separation of Mouse Serum Albumin and IgG

Figure 10:
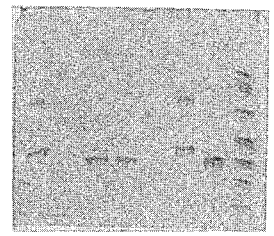
FIG. 10 illustrates SDS-gradient polyacrylamide gel electrophoresis of fractions recovered by O-gel chromatography of a mixture of mouse serum albumin and IgG.

Fifteen ml solution containing a mixture of 7.5 mg mouse serum albumin and 7.5 mg mouse immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 10, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH (containing IgG).

EXAMPLE 23

Separation of Pig Serum Albumin and IgG

Figure 11:
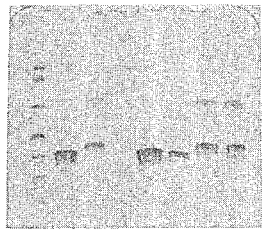
FIG. 11 illustrates SDS-gradient polyacrylamide gel electrophoresis of fractions recovered by O-gel chromatography of a mixture of pig serum albumin and IgG.

Fifteen ml solution containing a mixture of 7.5 mg pig serum albumin and 7.5 mg pig immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 11, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH 4 (containing IgG).

EXAMPLE 24

Separation of Rabbit Serum Albumin and IgG

Figure 12:
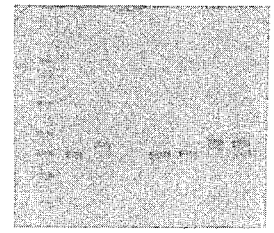
FIG. 12 illustrates SDS-gradient polyacrylamide gel electrophoresis of fractions recovered by O-gel chromatography of a mixture of rabbit serum albumin and IgG.

Fifteen ml solution containing a mixture of 7.5 mg rabbit serum albumin and 7.5 mg rabbit immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 12, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH 4 (containing IgG).

EXAMPLE 25

Separation of Rat Serum Albumin and IgG

Figure 13:
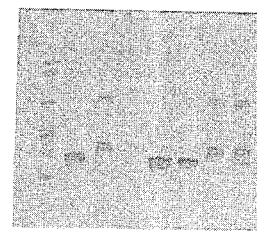
FIG. 13 illustrates SDS-gradient polyacrylamide gel electrophoresis of fractions recovered by O-gel chromatography of a mixture of rat serum albumin and IgG.
Figure 14:
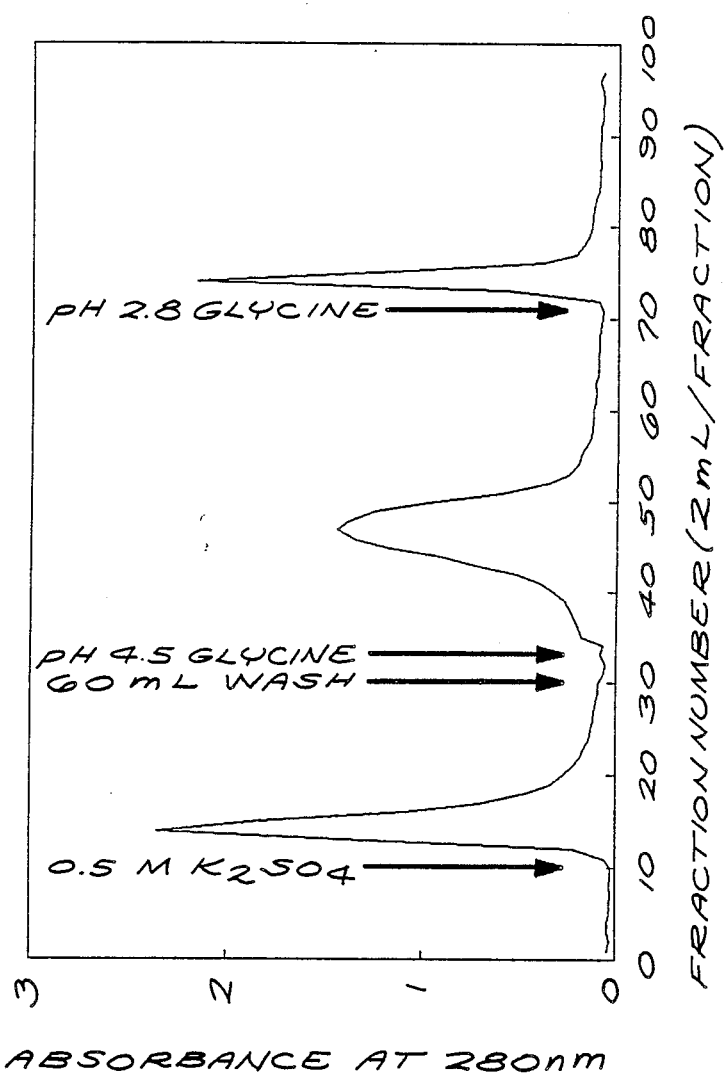
FIG. 14 is a chromatogram of the eluent recovered after treatment of diluted goat serum with DCTFP-DMAP activated, hydroxide treated gel.
Figure 15:
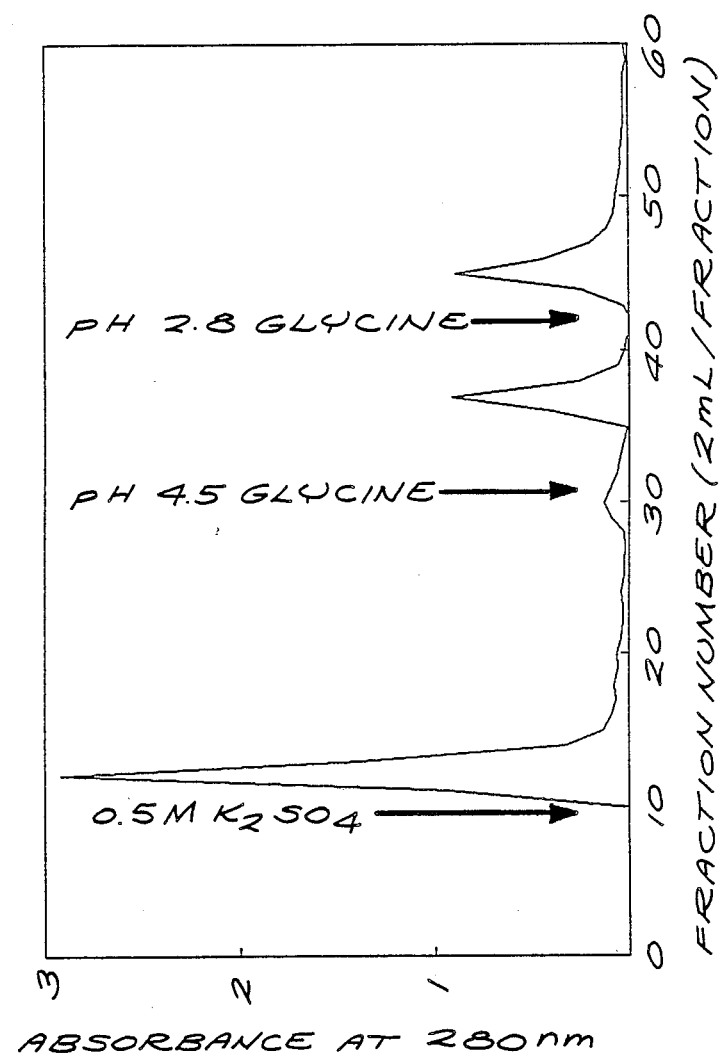
FIG. 15 is a chromatogram of the eluent recovered after treatment of diluted rabbit serum with DCTFP-DMAP activated, glycine treated gel.
Figure 16:
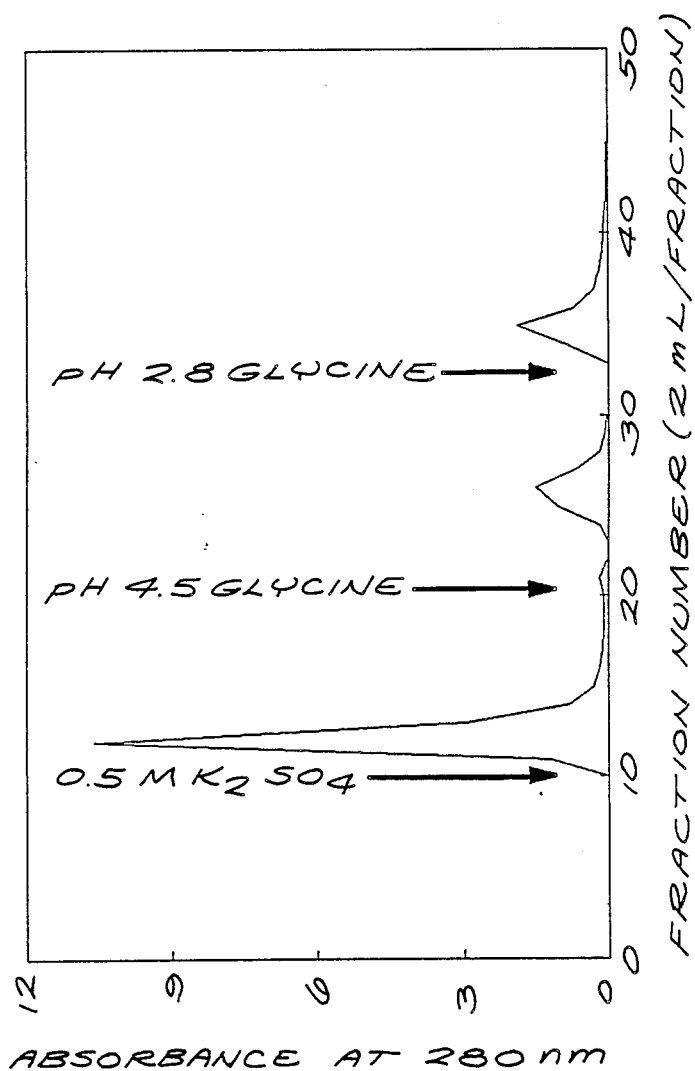
FIG. 16 is a chromatogram of the eluent recovered after treatment of diluted mouse serum with DCTFP-DMAP activated, glycine treated gel.
Figure 17:
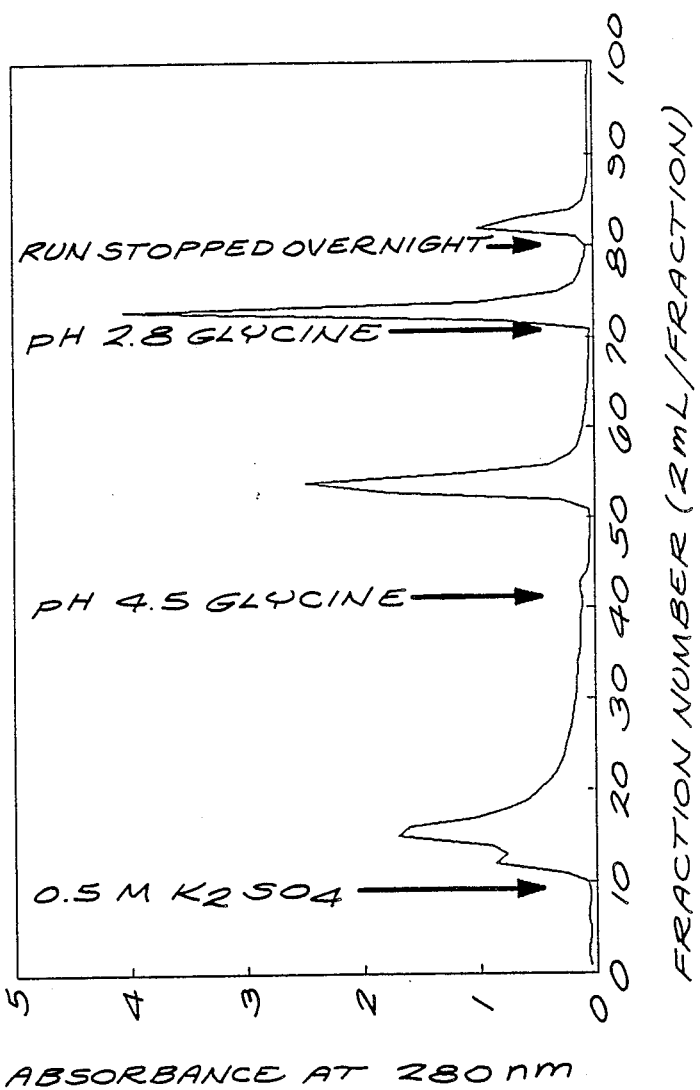
FIG. 17 is a chromatogram of the eluent recovered after treatment of diluted rabbit serum with DCTFP-DMAP activated, ethylene diamine treated gel.

Fifteen ml solution containing a mixture of 7.5 mg rat serum albumin and 7.5 mg rat immunoglobulin G in 20 mM sodium phosphate buffer, pH 7.5 was applied on a column of O-gel (2 ml) at a flow rate of 0.5 ml per minute. Fractions of 2 ml were collected. After washing the column with approximately 10 ml 20 mM sodium phosphate buffer, pH 7.5 serum albumin was eluted with 10 mM sodium phosphate, pH 7.4 and containing 150 mM NaCl. Subsequent to the elution of serum albumin, the immunoglobulin was eluted by using 0.1M glycine, pH 4. The completeness of the separation can be seen in the electrophoretogram of FIG. 13, wherein: column (1) comprises molecular weight markers; column (2) is an albumin sample; column (3) is an IgG sample; column (4) is the unbound, flow-through fraction; columns (5) and (6) are fractions eluted with 20 mM sodium phosphate, pH 7.4 containing 150 mM NaCl (containing albumin); and columns (7) and (8) are fractions eluted with 0.1M glycine, pH 4 (containing IgG).

EXAMPLE 26

Non-covalent binding of Non-serum Proteins

The gel of Example 7 (0.5 ml) was mixed with 3 ml protein solution (approximately 1 mg protein per ml) in a test tube and tumbled end-to-end for 15 minutes. After centrifugation, the supernatant was removed and the gel washed three times with 3 ml buffer per wash. The amount of protein in the supernatant and washes was determined and equated with the amount unbound. The results are shown in Table 2.

TABLE 2

Non-Covalent Binding of Non-Serum Proteins to O-Gel

| Protein | Protein Dissolved In | Amount of Protein Bound to 1 ml Gel (mg/ml gel) |
|---|---|---|
| Bovine Serum Albumin | P* | 3.5 |
|  | A** | 1.0 |
| Human IgG | P | 5.3 |
|  | A | 4.7 |
| Ribonuclease A | P | 0 |
|  | A | 0.8 |
| Fetuin | P | 2.1 |
|  | A | 2.2 |
| Lysozyme | P | 0 |
|  | A | 0.2 |
| Papain | P | 1.9 |
|  | A | 4.6 |
| Myoglobin | P | 0.6 |
|  | A | 0.6 |
| Transferrin | P | 4.9 |
|  | A | 1.1 |
| Pepsin | P | 6.0 |
|  | A | 5.6 |
| Trypsin | P | 3.7 |
|  | A | 1.8 |

*P: 20 mM sodium phosphate, pH 7.4
**A: 10% Ammonium sulfate solution.

EXAMPLE 27

Fractionation of Human Serum Proteins Using Ethylene Glycol Substituted Gel Prepared via Reaction Product of DMAP-DCTFP Adduct with Sepharose CL-4B The ethylene glycol substituted gel of Example 14 (7 ml) was packed in a column and washed with 20 mM sodium phosphate (pH 7.4). One ml human serum diluted with the same phosphate buffer was applied to the column at a flow rate of 1.25 ml per minute. The column was sequentially washed with the phosphate buffer, phosphate buffer containing 0.5M $K_2SO_4$, and 0.1M glycine (pH 5, 4 and 2.8). 3 ml fractions were collected and absorbance at 280 nm recorded. Four major fractions were obtained: serum albumin was collected in the first fraction peak, while immunoglobulins and other serum proteins were collected in the subsequent three fractions.

EXAMPLE 28

Fractionation of Non-Human Serum Proteins

Following the general procedure described in Example 27, various non-human serum samples were also successfully fractionated using substituted gels prepared in accordance with the present invention. The serum samples and DCTFP-DMAP activated gel treatment agents (i.e., ligands) employed are reported in Table 3; the corresponding chromatograms for the samples identified in Table 3 are illustrated in FIGS. 14–17. In each instance, the column containing the indicated gel was sequentially washed after introduction of the serum sample with the phosphate buffer, phosphate buffer containing 0.5M $K_2SO_4$, 0.1M glycine at pH 4.5 and 0.1M glycine at pH 2.8.

TABLE 3

Fractionation of Non-Human Sera

| Species | Ligand | Chromatogram Figure |
|---|---|---|
| Goat | Hydroxide (NaOH treated) | 14 |
| Mouse | Glycine | 15 |
| Rabbit | Glycine | 16 |
| Rabbit | Ethylene Diamine | 17 |

EXAMPLE 29

Activation of FRACTOGEL TSK HW 75F with 3,5-Dinitro-2-chloropyridine (CDNP)

The procedure of Example 1 was repeated using FRACTOGEL TSK HW 75F, a porous, semi-rigid spherical gel synthesized from hydrophilic vinyl polymer and composed exclusively of C,H and O atoms, supplied by E. Merck, Darmstadt, Germany as the matrix and 3,5-dinitro-2-chloropyridine (CDNP) as the activating agent.

Other activating agents used were 2,3,5-trichloropyridine (TCP); 2,6-difluoropyridine (DFP); 2-chloro-5-trifluoromethylpyridine (CTFMP); 2,3,5,6-tetrafluoro-4-methylpyridine (TFMP) and 2,3,5,6-tetrafluoropyridine (TFP).

EXAMPLE 30

Coupling of Bovine Serum Albumin (BSA) to Activated Gel

One volume of activated gel prepared as in Examples 1, 2 and 29 was washed with 10 volumes distilled water. Immediately after washing, one volume of activated gel was added to one to two volumes BSA and the suspension was tumbled at room temperature for 20 hours. The unreacted activated groups were deactivated by reacting the gel with equal volume 0.2M ethanolamine in 0.1M Tris, pH 9 at room temperature for 8 hours. The BSA solution was prepared in buffer with no amino or other nucleophilic groups. Acetate buffer was used for pH 1–4; phosphate buffer was used for pH 5–7 and bicarbonate buffer was used for pH 8–10.

The amounts of BSA coupled at various pH's using various activators and gels are shown in Table 4.

TABLE 4

| | | BSA Coupled (mg BSA/ml gel) Coupling pH | |
|---|---|---|---|
| Activator | Gel | 4 | 8 |
| Pentafluoro-pyridine | Fractogel[a] | 20.6 | 28.2 |
|  | Sepharose[b] | 4.8 | 24.1 |
| 3,5-Dichloro-2,4,6-trifluoro- | Fractogel | 30.0 | 24.7 |
|  | Sepharose | 32.8 | 68.9 |

TABLE 4-continued

| Activator | Gel | BSA Coupled (mg BSA/ml gel) Coupling pH | |
|---|---|---|---|
| | | 4 | 8 |
| pyridine | | | |
| 3,5-Dinitro-2-chloro-pyridine | Fractogel | 14.7 | 26.3 |
| | Sepharose | 0.5 | 6.6 |
| 2,3,5-Trichloro-pyridine | Sepharose | 0.3 | 2.7 |
| 2,6-Difluoro-pyridine | Fractogel | 0.6 | 0.5 |
| | Sepharose | — | 0.1 |
| 2-Chloro-5-trifluoromethyl-pyridine | Sepharose | — | 0.15 |
| 2,3,5,6-Tetrafluoro-4-methyl-pyridine | Sephacryl[c] | — | 0.4 |
| 2,3,5,6-Tetrafluoropyridine | Sepharose | — | 0.9 |

[a]Fractogel TSK HW 75F, trademark of E. Merck.
[b]Sepharose Cl-4B, trademark of Pharmacia.
[c]Sephacryl S-300 a copolymer of dextran and acrylamide, trademark of Pharmacia

EXAMPLE 31

Coupling of β-Galactosidase to DCTFP-Activated SEPHAROSE CL-4B

DCTFP activated SEPHAROSE CL-4B gel (2.5 ml) was washed with 25 ml distilled water. The filtered gel was added to 1 ml β-galactosidase solution (5 mg enzyme in 1 ml PBS). The gel suspension was tumbled at room temperature for 2 hours. The gel was washed twice with 5 ml PBS, four times with 5 ml PBS with 0.5 ml NaCl and two times with 5 ml PBS. The immobilized enzyme having 14 mg enzyme bound per milliliter of gel with 40% retention of enzyme activity was stored in PBS at 4° C.

EXAMPLE 32

Immobilization of Pepsin to SEPHAROSE CL-4B Activated by 3,5-Dichloro-2,4,6-trifluoropyridine (DCTFP)

Pepsin (70 mg) purified from porcine stomach mucosa with a specific activity of 3100 units per milligram of protein was dissolved in 2 ml 0.1M sodium acetate, pH 3.4. Then 5 ml of DCTFP-activated SEPHAROSE CL-4B gel was added to the enzyme solution and was allowed to tumble at room temperature for 20 hours. The immobilized pepsin was washed with 50 ml 0.1M sodium acetate, pH 3.5; 50 ml 0.1M sodium acetate, pH 3.5, containing 0.5M NaCl and 50 ml 0.05M HCl. The immobilized pepsin was then suspended in 50 ml 0.5M ethanolamine in acetate buffer, pH 3.5 and was tumbled at 4° C. for 5 hours. After filtering off the supernatant, the immobilized enzyme was resuspended in 50 ml 0.1M sodium acetate, pH 3.5 and was tumbled at room temperature for 15 minutes and washed with 50 ml 0.05M HCl. The immobilized pepsin was stored in 10 ml 0.05M HCl with 50% glycerol and 0.1% sodium azide at 4° C.

The immobilized pepsin was found to have an activity of 17,635 units per milliliter of gel and contained 6 mg protein per milliliter of gel.

EXAMPLE 33

Coupling of Ribonucleic Acid (RNA) to DCTFP Activated SEPHAROSE CL-4B Gel

One volume of DCTFP-activated SEPHAROSE CL-4B gel was washed with 10 volumes distilled water. Immediately after washing, 0.5 ml activated gel was added to 2 ml solution of tritium labeled calf thymus ribonucleic acid (10 mg H-3 RNA per ml in 0.05M sodium bicarbonate, pH 8.5) and the suspension was tumbled at room temperature for 20 hours. The gel was successively washed with 8 ml FBS, 1M NaCl, 8M urea, 10% sodium dodecyl sulfate and distilled water. The immobilized RNA gel (0.25 ml) was mixed with 4 ml liquid scintillation fluid and then the radioactivity was counted in a β-counter. It was found that 2 mg of RNA was bound to 1 mg gel.

EXAMPLE 34

Preparation of Immobilized Protein A Gel

PFP-activated SEPHAROSE CL-4B (5 ml) was suspended in 5 ml Protein A solution containing 10 mg Protein A per ml 0.05M NaHCO$_3$, pH 8.5. The gel suspension was tumbled at room temperature for 24 hours. The gel was washed with 50 ml 0.05M NaHCO$_3$, 50 ml 0.5M NaCl and 50 ml 0.05M NaHCO$_3$. The washed gel was tumbled in 50 ml 0.1M ethanolamine in 0.05M NaHCO$_3$, pH 8.5 at room temperature for 5 hours. The immobilized Protein A gel was washed with 25 ml PBS containing 2M NaCl, 25 ml 1M glycine, pH 2.8 and 25 ml PBS.

EXAMPLE 35

Affinity Chromatography and Purification of Human IgG

Figure 18:
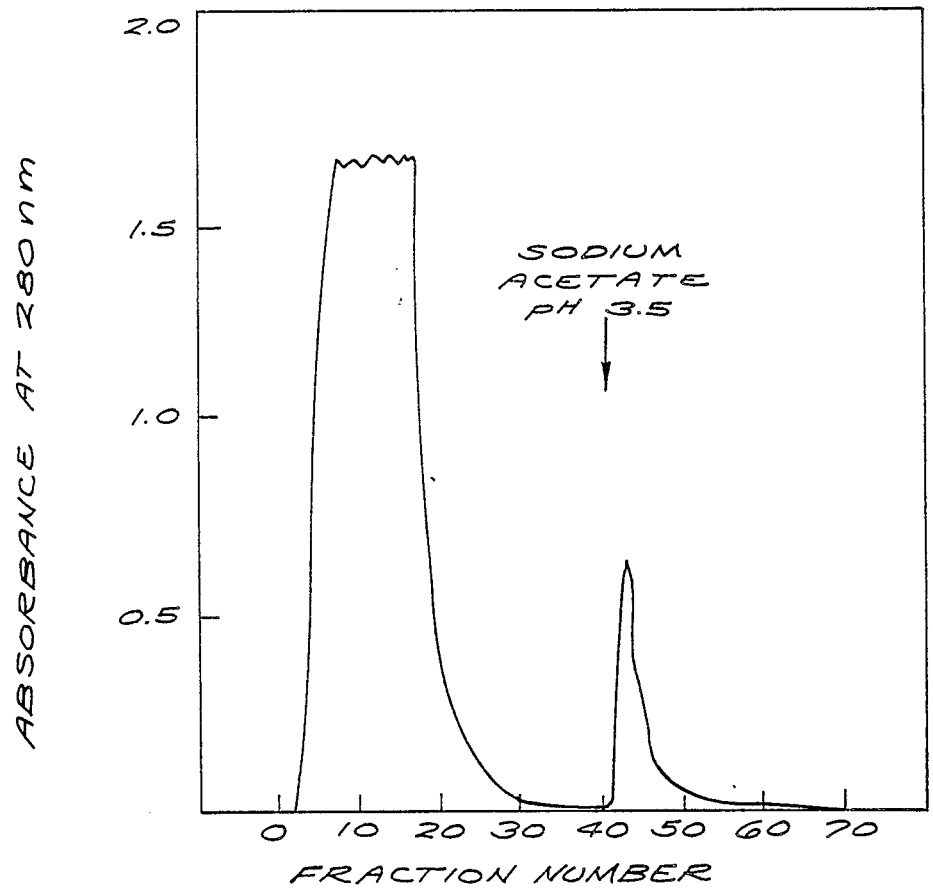
FIG. 18 is an elution curve illustrating the affinity chromatography of IgG from human serum using Protein A bound to pentafluoropyridine (PFP)-activated Sepharose CL-4B as the affinity matrix.

Immobilized Protein A gel (1 ml) prepared according to the procedure of Example 34 was packed into a small column (0.8×2.3 cm$^2$). Human serum (3 ml) diluted with 2 volumes (6 ml) PBS, pH 7.4 was applied to the column. The column was washed with 20 ml PBS and the bound IgG was eluted with 5 ml 0.1M sodium acetate, pH 3.5. The results are shown in FIG. 18. A quantity of 14.7 mg human IgG was isolated per milliliter of gel.

EXAMPLE 36

Coupling of Bovine Serum Albumin (BSA) to Activated Paper

Disks of activated paper (diameter: 1.3 cm) prepared according to the method of Example 4 were each placed in 1 ml I-125 labeled BSA (40 mg/ml in 0.5M sodium bicarbonate, pH 8.5) in a test tube. The tubes were tumbled at room temperature for 20 hours. Each disk was washed twice with 10 ml of each of the following solutions: distilled water, 1M NaCl, 1.5M KSCN, 8M urea, phosphate buffered saline (PBS), 10% sodium dodecyl sulfate (SDS) and distilled water. The radioactivity of each disk was measured and the quantity of BSA bound to each disk was determined. It was found that 6 mg BSA could be bound to 1 square centimeter of paper after 30 minutes activation. Very little of the bound BSA could be eluted by treating the paper with chaotropic solutions such as 15M KSCN or 8M urea and a strong detergent such as 10% SDS solution.

EXAMPLE 37

Binding of I-125 Labeled Bovine Serum Albumin (BSA) to DCTFP-activated Nylon Membrane DCTFP-activated Nylon membrane (1 cm×1 cm) prepared according to the procedure of Example 5 was suspended in 2 ml I-125 labeled BSA (40 mg/ml) and tumbled at room temperature for 20 hours. The membrane was successively washed with 8 ml PBS, 1M NaCl, 1.5M KSCN, 8M urea, 10% SDS and distilled water. It was found that 2.80 mg I-125 BSA was bound per square centimeter of membrane compared to 0.85 mg/cm² for a control unactivated membrane.

EXAMPLE 38

Ligand Leakage Experiments

The experiments were conducted by using I-125 labeled BSA as the ligand coupled to DCTFP activated SEPHAROSE CL-4B as the activated carrier. After extensive washing to remove the unbound ligand as much as possible, the gel containing immobilized I-125 labeled BSA was packed into a column (1×10 cm²) and was equilibrated at room temperature with 0.01M Tris, pH 9 containing 0.1M ethanolamine. Immediately 10 ml column effluent was collected and the amount of I-125 labeled BSA ligand was quantified. The column outlet was clamped and left at room temperature in the above-mentioned ethanolamine-Tris solution. After 24 hours, 10 ml of equilibrating solution was allowed to pass through the column and the eluate was measured and the amount of ligand leaked out of the gel was calculated. Less than 0.75% of the total immobilized I-125 labeled BSA could be leaked out of the gel during any 24-hour incubation period.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What I claim is:

1. A process for activating a polymeric substance comprising:

reacting a polymeric substance containing at least one nucleophilic group with a substituted 2-halopyridine of the formula:

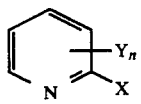

wherein X is F, Cl or Br; Y is F, Cl, Br, NO₂, CH₃ or CF₃; and n is 1 to 4; and wherein, when n is greater than 1, the substituents designated by Y may be the same or different, at least one of said substituents being an electron withdrawing group; and recovering a polymeric product wherein at least some of the nucleophilic groups of the polymer have been activated by reaction with said 2-halopyridine.

2. A process according to claim 1 wherein the reaction is conducted in the presence of a slight excess of a tertiary amine and in a polar organic solvent.

3. A process according to claim 1 wherein said polymeric substance is selected from the group consisting of polysaccharides, polyethylene glycol, polyvinyl alcohol, polyhydroxyethyl methacrylate, nylon and silica particles to the surface of which have been bonded groups containing at least one nucleophilic group bonded to a carbon atom.

4. A process according to claim 1 wherein said substituted 2-halopyridine is selected from the group consisting of pentafluoropyridine, pentachloropyridine, 3,5-dichloro-2,4,6-trifluoropyridine, 3,5-dinitro-2-chloropyridine, 2,3,5-trichloropyridine, 2,6-difluoropyridine, 2-chloro-5-trifluoromethylpyridine, 2,3,5,6-tetrafluoro-4-methylpyridine and 2,3,5,6-tetrafluoropyridine.

5. A process for preparing a compound of formula I(a) or I(b)

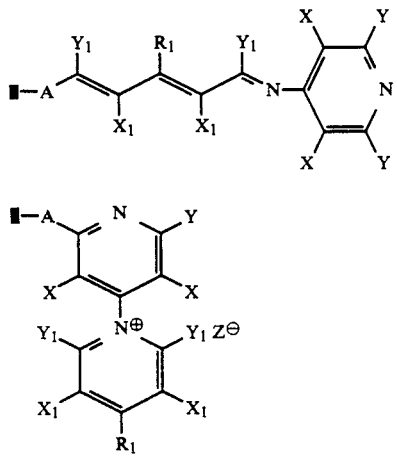

wherein

A is O, S or NR, in which R is hydrogen or substituted or unsubstituted alkyl, aryl or aralkyl;

each X is independently selected from the group consisting of halogen, trihalomethyl and nitro;

each Y is independently selected from the group consisting of halogen, hydroxyl, amino and —A₁R₄, in which A₁ is O, S or NR₅, R₄ is substituted or unsubstituted alkyl, aryl, or aralkyl, and R₅ is hydrogen or substituted or unsubstituted alkyl, aryl or aralkyl, with the proviso that at least one Y in Formula I (a) or Y in Formula I(b) is not halogen;

each of X₁ is hydrogen or substituted or unsubstituted alkyl, aryl or aralkyl;

at least one Y₁ is hydrogen and the other is hydrogen or substituted or unsubstituted alkyl, aryl or aralkyl;

R₁ is hydrogen, substituted or unsubstituted alkyl, aryl or aralkyl, or —NR₂R₃, in which R₂ and R₃ are the same or different and are substituted or unsubstituted alkyl, aryl or aralkyl; and ▌ is a polymer, which comprises reacting together (a) a halogen-substituted pyridine of formula II:

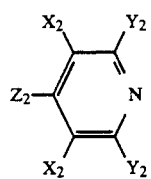

wherein each X₂ is independently selected from the group consisting of halogen, trihalomethyl and NO₂;

at least one Y₂ is halogen and the other Y₂ is selected from the group consisting of halogen and —A₁R₄, in which $A_1$ is O, S or $NR_5$, $R_4$ is substituted or unsubstituted alkyl, aryl, or aralkyl, and $R_5$ is substituted or unsubstituted alkyl, aryl or aralkyl; and $Z_2$ is a suitable leaving group; and (b) a pyridine base of formula III:

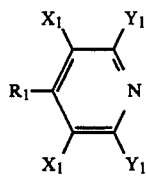

wherein
each of $X_1$ is hydrogen or substituted or unsubstituted alkyl, aryl or aralkyl;

at least one $Y_1$ is hydrogen and the other $Y_1$ is hydrogen or substituted or unsubstituted alkyl, aryl or aralkyl; and $R_1$ is hydrogen, substituted or unsubstituted alkyl, aryl or aralkyl, or $-NR_2R_3$, in which $R_2$ and $R_3$ are the same or different and are substituted or unsubstituted alkyl, aryl or aralkyl, and (c) a nucleophile-containing polymer, at a temperature in the range of about 0° to about 90° over a period of time of about 10 minutes to about 20 hours in an organic solvent to form a compound of formula IV(a) or IV(b)

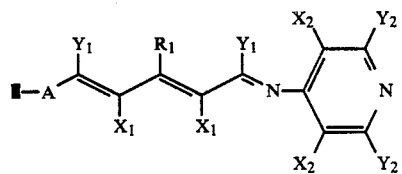

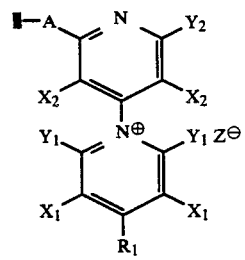

wherein the substituents are as previously defined, and where both $Y_2$ in Formula IV(a) are halogen or $Y_2$ in Formula IV(b) is halogen, further reacting said compound of formula IV(a) or IV(b) with hydroxide ions or a compound of formula VI:

$R_6-B-R_7$ wherein B is a substituted or unsubstituted alkyl, aryl or aralkyl moiety of 2 to about 10 carbon atoms; and each of $R_6$ and $R_7$ is $-OH$, $-SH$ or $-NR_8R_9$, in which each of $R_8$ and $R_9$ is hydrogen or substituted or unsubstituted alkyl, aryl or aralkyl, at a temperature of about 0° to about 100° C. for about 10 minutes to about 20 hours in a suitable solvent.

6. A process for preparing a compound of formula I(a) or I(b)

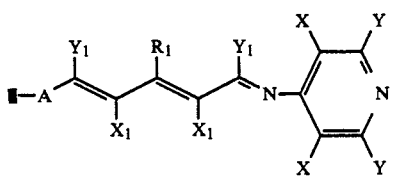

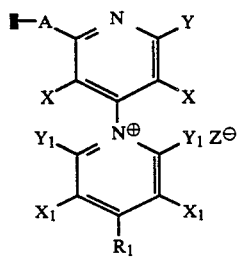

wherein
A is O, S or NR, in which R is hydrogen or substituted or unsubstituted alkyl, aryl or aralkyl;

each X is independently selected from the group consisting of halogen, trihalomethyl and nitro;

each Y is independently selected from the group consisting of halogen, hydroxyl, amino and $-A_1R_4$, in which $A_1$ is O, S or $NR_5$, $R_4$ is substituted or unsubstituted alkyl, aryl, or aralkyl, and $R_5$ is hydrogen or substituted or unsubstituted alkyl, with (b) a pyridine base of formula III:

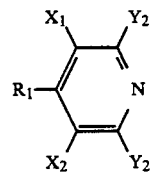

wherein
each of $X_1$ is hydrogen or substituted or unsubstituted alkyl, aryl or aralkyl;

at least one $Y_1$ is hydrogen and the other $Y_1$ is hydrogen or substituted or unsubstituted alkyl, aryl or aralkyl; and $R_1$ is hydrogen, substituted or unsubstituted alkyl, aryl or aralkyl, or $-NR_2R_3$, in which $R_2$ and $R_3$ are the same or different and are substituted or unsubstituted alkyl, aryl or aralkyl, at a temperature in the range of about 0° to about 90° over a period of time of about 10 minutes to about 20 hours in an organic solvent to form an intermediate of formula V

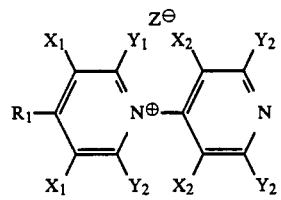

wherein
Z is a suitable counterion; and (2) reacting said intermediate of formula V with (c) a nucleophile containing polymer, under basic conditions in a suitable organic solvent to form a compound of formula IV(a) or IV(b)

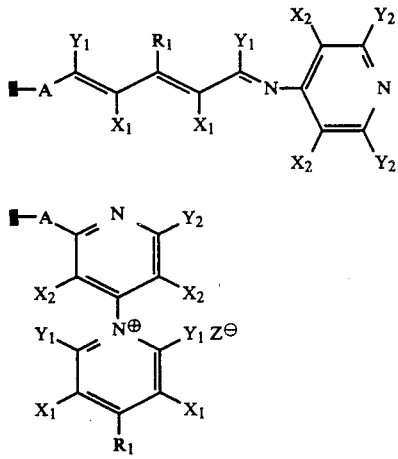

wherein the substituents are as previously defined, and where both $Y_2$ in Formula IV(a) are halogen or $Y_2$ in Formula IV(b) is halogen, further reacting said compound of formula IV(a) or IV(b) with hydroxide ions or a compound of formula VI:

$$R_6-B-R_7$$

wherein B is a substituted or unsubstituted alkyl, aryl or aralkyl moiety of 2 to about 10 carbon atoms; and each of $R_6$ and $R_7$ is —OH, —SH or —$NR_8R_9$, in which each of $R_8$ and $R_9$ is hydrogen or substituted or unsubstituted alkyl, aryl or aralkyl, at a temperature of about 0° to about 100° C. for about 10 minutes to about 20 hours in a suitable solvent.

7. An activated polymer capable of forming covalent linkages with a nucleophilic ligand which comprises: a nucleophilic group containing polymer wherein at least some of the nucleophilic groups have been activated by reaction with a substituted 2-halopyridine of the formula:

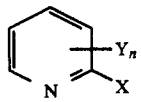

wherein X is F, Cl or Br; Y is F, Cl, Br, $NO_2$, $CH_3$ or $CF_3$; and n is 1 to 4; and wherein, when n is greater than 1, the substituents designated by Y may be the same or different, at least one of said substituents being an electron withdrawing group.

8. A reaction product of
(a) a nucleophile-containing polymeric gel with
(b) a halogen-substituted pyridine of formula II:

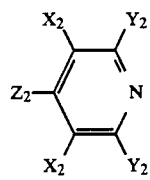

wherein each $X_2$ is independently selected from the group consisting of halogen, trihalomethyl and nitro; at least one $Y_2$ is halogen and the other $Y_2$ is selected from the group consisting of halogen and —$A_1R_4$, in which $A_1$ is O, S or $NR_5$, $R_4$ is substituted or unsubstituted alkyl, aryl, or aralkyl, and $R_5$ is substituted or unsubstituted alkyl, aryl or aralkyl; and
$Z_2$ is a suitable leaving group; and
(c) a pyridine base of formula III:

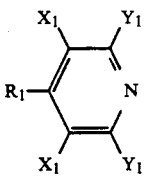

wherein
each of $X_1$ is hydrogen or substituted or unsubstituted alkyl, aryl or aralkyl;
at least one $Y_1$ is hydrogen and the other $Y_1$ is hydrogen or substituted or unsubstituted alkyl, aryl or aralkyl; and
$R_1$ is hydrogen, substituted or unsubstituted alkyl, aryl or aralkyl, or —$NR_2R_3$, in which $R_2$ and $R_3$ are the same or different and are substituted or unsubstituted alkyl, aryl or aralkyl.

9. A reaction product according to claim 8, wherein said halogen-substituted pyridine is selected from the group consisting of 3,5-dichloro-2,4,6-trifluoropyridine, pentafluoropyridine and pentachloropyridine.

10. A reaction product according to claim 8, wherein said pyridine base is 4-dimethylaminopyridine.

11. A reaction product according to claim 8, wherein —$A_1R_4$ in formula II is selected from the group consisting of —$SCH_2CH_2OH$, —$OCH_2CH_2OH$, —$NHCH_2CH_2OH$, —$NHCH_2COOH$, —$SCH_2CH_2COOH$, —$NHCH(COOH)CH_2CH_2COOH$, —$SCH_2CHOHCHOHCH_2SH$, —$SCH_2CHOHCHOHCH_2SCH_2CONH_2$, —$NHCH_2CH_2NH_2$ and —$NHCH_2CH_2OH$.

12. A reaction product according to claim 8, wherein at least one $Y_2$ in formula II is halogen and said reaction product is in turn reacted with hydroxide ions or a compound of formula VI $$R_6-B-R_7$$

wherein B is a substituted or unsubstituted alkyl, aryl or aralkyl moiety of 2 to about 10 carbon atoms; and each of $R_6$ and $R_7$ is —OH, —SH or —$NR_8R_9$, in which each of $R_8$ and $R_9$ is hydrogen or substituted or unsubstituted alkyl, aryl or aralkyl.

13. A reaction product according to claim 12, wherein said compound of formula VI is selected from the group consisting of ethanolamine, ethylene glycol, 2-mercaptoethanol, mercaptopropionate, dithiothreitol, alkylenediamines and amino acids.

14. A reaction product according to claim 8, wherein said polymer contains at least one nucleophilic group selected from the group consisting of hydroxyl, amino and sulfhydryl, said nucleophilic group being bonded to a carbon atom and available for activation and coupling.

15. A reaction product according to claim 14, wherein said polymer is selected from the group consisting of polysaccharides, polyethylene glycol, polyvinyl alcohol, polyhydroxyethyl methacrylate and nylon.

16. A reaction product according to claim 15, wherein said polymer is in a solid form selected from the group consisting of gels, beads, fibers, fabrics and membranes.

17. A compound of formula I(a) or I(b):

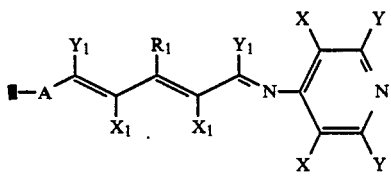

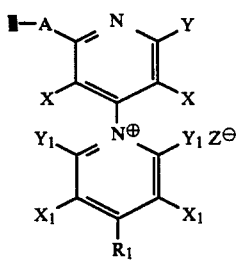

wherein
A is O, S or NR, in which R is hydrogen or substituted or unsubstituted alkyl, aryl or aralkyl;
each X is independently selected from the group consisting of halogen, trihalomethyl and nitro;
each Y is independently selected from the group consisting of halogen, hydroxyl, amino and $-A_1R_4$, in which $A_1$ is O, S or $NR_5$, $R_4$ is substituted or unsubstituted alkyl, aryl, or aralkyl, and $R_5$ is hydrogen or unsubstituted or unsubstituted alkyl, aryl or aralkyl, with the proviso that at least one Y in Formula I(a) or Y in Formula I(b) is not halogen; and
each of $X_1$ is hydrogen or substituted or unsubstituted alkyl, aryl or aralkyl;
at least one $Y_1$ is hydrogen and the other is hydrogen or substituted or unsubstituted alkyl, aryl or aralkyl;
$R_1$ is hydrogen, substituted or unsubstituted alkyl, aryl or aralkyl, or $-NR_2R_3$, in which $R_2$ and $R_3$ are the same or different and are substituted or unsubstituted alkyl, aryl or aralkyl; and
is a polymer.

18. A compound according to claim 17, wherein Y is selected from the group consisting of hydroxyl, $-SCH_2CH_2OH$, $-CH_2CH_2OH$, $-NHCH_2COOH$, $-SCH_2CH_2COOH$, $-NHCH(COOH)CH_2CH_2COOH$, $-SCH_2CHOHCHOHCH_2SH$, $-SCH_2CHOHCHOHCH_2SCH_2CONH_2$, $-NHCH_2CH_2NH_2$ and $-NHCH_2CH_2OH$.

19. A compound according to claim 17, wherein X is Cl or F.

20. A compound according to claim 17, wherein $R_1$ is $-N(CH_3)_2$.

21. A compound according to claim 17, wherein A is O.

22. A process of covalently binding an organic ligand that contains at least one substituent selected from the group consisting of primary amino groups, secondary amino groups, primary hydroxyl groups, secondary hydroxyl groups and sulfhydryl groups to a polymeric substance containing at least one nucleophilic group comprising the steps of:

(1) first forming an activated polymer by reacting a polymeric substance containing at least one nucleophilic group with a substituted 2-halopyridine of the formula:

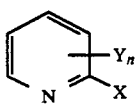

wherein X is F, Cl or Br; Y is F, Cl, Br, $NO_2$, $CH_3$ or $CF_3$ and n is 1 to 4; and wherein, when n is greater than 1, the substituents designated by Y may be the same or different, at least one of said substituents being an electron withdrawing group; wherein at least one reacting nucleophilic group of said polymeric substance is bonded to a carbon atom in the polymeric substance; and then (2) reacting said activated polymer directly with said organic ligand.

23. A process according to claim 22 wherein said organic ligand is selected from the group consisting of $\beta$-galactosidase, pepsin, bovine serum albumin, nucleic acids, ribonucleic acids and Protein A.

24. A product of coupling an organic ligand containing at least one substitutent selected from the group consisting of primary amino groups, secondary amino groups, primary hydroxyl groups, secondary hydroxyl groups and sulfhydryl groups to a polymeric substance containing at least one nucleophilic group, prepared according to the process of claim 22.

25. An affinity chromatographic method for isolating and purifying a biologically active material which comprises:

(1) first forming an activated polymer by reacting a polymeric substance containing at least one nucleophilic group with a substituted 2-halopyridine of the formula:

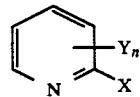

wherein X is F, Cl, or Br; Y is F, Cl, Br, $NO_2$, $CH_3$, or $CF_3$ and n is 1 to 4; and wherein, when n is greater than 1, the substituent designated by Y may be the same or different, at least one of said substituents being an electron withdrawing group; wherein at least one reacting nucleophilic group of said polymeric substance is bonded to a carbon atom in the polymeric substance;

(2) reacting said activated polymer with Protein A;

(3) contacting the resulting Protein A reacted activated polymer with a mixture of serum proteins to absorb a selected serum protein which has an affinity for Protein A upon said Protein A reacted activated polymer; and (4) eluting a purified selected serum protein from said product.

26. A method according to claim 25 wherein said mixture of serum proteins is human serum and said selected serum protein is human IgG.

27. A compound of formula V

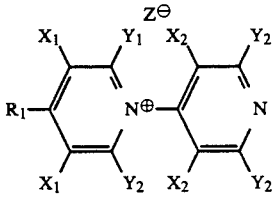

wherein
- each $X_1$ is hydrogen or substituted or unsubstituted alkyl, aryl or aralkyl;
- at least one $Y_1$ is hydrogen and the other $Y_1$ is hydrogen or substituted or unsubstituted alkyl, aryl or aralkyl;
- $R_1$ is substituted or unsubstituted alkyl, aryl or aralkyl, or $-NR_2R_3$, in which $R_2$ and $R_3$ are the same or different and are substituted or unsubstituted alkyl, aryl or aralkyl;
- each $X_2$ is independently selected from the group consisting of halogen, trihalomethyl and $NO_2$;
- at least one $Y_2$ is halogen and the other $Y_2$ is selected from the group consisting of halogen, hydroxyl, amino and $-A_1R_4$, in which Al is O, S or $NR_5$, $R_4$ is substituted or unsubstituted alkyl, aryl, or aralkyl, and $R_5$ is hydrogen or substituted or unsubstituted alkyl, aryl or aralkyl; and
- Z is a suitable counterion.

28. A method for preparing a compound of formula I(a) or I(b)

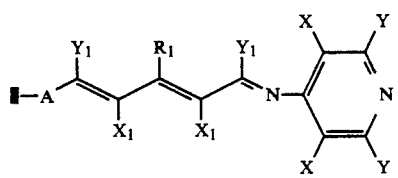

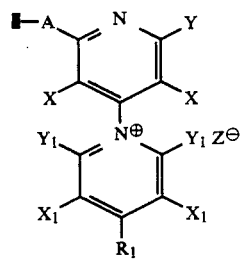

wherein
- A is O, S or NR, in which R is hydrogen or substituted or unsubstituted alkyl, aryl or aralkyl;
- each X is independently selected from the group consisting of halogen, trihalomethyl and nitro;
- at least one Y in Formula I(a) is hydroxyl and the other Y is hydroxyl or halogen, or Y in Formula I(b) is hydroxyl;
- each of $X_1$ is hydrogen or substituted or unsubstituted alkyl, aryl or aralkyl;
- at least one $Y_1$ is hydrogen and the other is hydrogen or substituted or unsubstituted alkyl, aryl or aralkyl;
- $R_1$ is hydrogen, substituted or unsubstituted alkyl, aryl or aralkyl, or $-NR_2R_3$, in which $R_2$ and $R_3$ are the same or different and are substituted or unsubstituted alkyl, aryl or aralkyl; and is a polymer, which comprises reacting an intermediate of formula IV(a) or Iv(b)

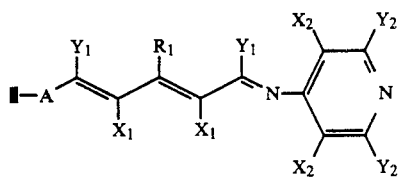

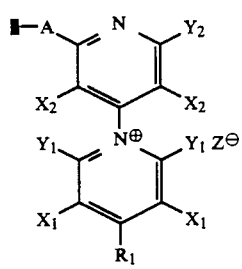

wherein
- each $X_1$ is hydrogen or substituted or unsubstituted alkyl, aryl or aralkyl;
- $Y_1$ is hydrogen or substituted or unsubstituted alkyl, aryl or aralkyl;
- $R_1$ is hydrogen, substituted or unsubstituted alkyl, aryl or aralkyl, or $-NR_6R_7$, in which $R_6$ and $R_7$ are the same or different and are substituted or unsubstituted alkyl, aryl or aralkyl;
- each $X_2$ is independently selected from the group consisting of halogen, trihalomethyl and $NO_2$;
- both $Y_2$ in Formula IV(a) are halogen or $Y_2$ in Formula IV(b) is halogen; and
- Z is a suitable counterion, with a source of hydroxide ions.

29. A method according to claim 28, wherein said source of hydroxide ions is a solution of a base selected from the group consisting of NaOH, $NaHCO_3$ and $Na_2CO_3$.

30. A method for recovering at least one organic material from a composition comprising same by affinity chromatography, which comprises
(1) contacting said organic material in a suitable buffer solution with a compound of formula I(a) or I(b)

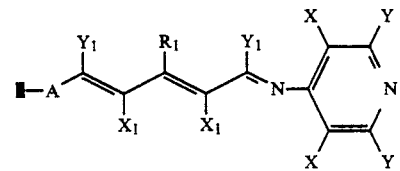

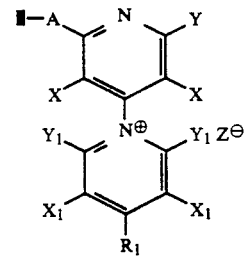

wherein

A is O, S or NR, in which R is hydrogen or substituted or unsubstituted alkyl, aryl or aralkyl;

each X is independently selected from the group consisting of halogen, trihalomethyl and nitro;

each Y is independently selected from the group consisting of hydroxyl, amino and $-A_1R_4$, in which $A_1$ is O, S or $NR_5$, $R_4$ is substituted or unsubstituted alkyl, aryl, or aralkyl, and $R_5$ is hydrogen or substituted or unsubstituted alkyl, aryl or aralkyl; and each of $X_1$ is hydrogen or substituted or unsubstituted alkyl, aryl or aralkyl;

at least one $Y_1$ is hydrogen and the other is hydrogen or substituted or unsubstituted alkyl, aryl or aralkyl;

$R_1$ is hydrogen, substituted or unsubstituted alkyl, aryl or aralkyl, or $-NR_2R_3$, in which $R_2$ and $R_3$ are the same or different and are substituted or unsubstituted alkyl, aryl or aralkyl; and is a polymer, under conditions effective to achieve non-covalent binding of said organic material with said compound of formula I(a) or I(b), thereby forming a bound complex; and (2) separating unbound components of said composition from said bound complex.

31. A method according to claim 39, further comprising (3) separating said organic material from said complex.

32. A method according to claim 30, wherein said organic material is an immunoglobulin.

33. A method according to claim 32, wherein said immunoglobulin is IgG selected from the group consisting of human, bovine, chicken, goat, mouse, pig, rabbit and rat IgG.

34. A method according to claim 30, wherein said organic material is serum albumin.

35. A method according to claim 34, wherein said serum albumin is selected from the group consisting of human, bovine, chicken, goat, mouse, pig, rabbit and rat serum albumin.

36. A method according to claim 30, wherein said composition comprises whole serum.

37. A method according to claim 30, wherein said contacting is carried out in a chromatography column, and further comprising recovering said organic material in substantially purified form by elution from said chromatography column.

38. A method according to claim 30, wherein said organic material is a nucleic acid.

* * * * *